(12) United States Patent
Mori et al.

(10) Patent No.: US 7,470,246 B2
(45) Date of Patent: Dec. 30, 2008

(54) CENTRIFUGAL BLOOD PUMP APPARATUS

(75) Inventors: Takehisa Mori, Kanagawa (JP); Mitsutoshi Yaegashi, Kanagawa (JP); Takayoshi Ozaki, Shizuoka (JP)

(73) Assignees: Terumo Kabushiki Kaisha, Shibuya-Ku, Tokyo (JP); NTN Corporation, Osaka-Shi, Osaka (JP)

( * ) Notice: Subject to any disclaimer, the term of this patent is extended or adjusted under 35 U.S.C. 154(b) by 566 days.

(21) Appl. No.: 10/736,610

(22) Filed: Dec. 17, 2003

(65) Prior Publication Data

US 2004/0143151 A1      Jul. 22, 2004

(30) Foreign Application Priority Data

Dec. 17, 2002   (JP)   ............... 2002-365039

(51) Int. Cl.
*A61M 37/00*    (2006.01)
*F04B 17/00*    (2006.01)
*A61M 1/00*     (2006.01)

(52) U.S. Cl. .......................... 604/6.11; 600/16; 422/44; 417/410.1; 417/420

(58) Field of Classification Search ................ 604/4.01, 604/5.01, 6.11, 151, 131; 210/645; 422/44; 600/16; 417/321, 356, 420, 44.1, 410.1, 417/423.1
See application file for complete search history.

(56) References Cited

U.S. PATENT DOCUMENTS

| | | | | |
|---|---|---|---|---|
| 5,947,703 A | | 9/1999 | Nojiri et al. | |
| 5,965,089 A | * | 10/1999 | Jarvik et al. | 422/44 |
| 6,074,180 A | * | 6/2000 | Khanwilkar et al. | 417/356 |
| 6,155,969 A | * | 12/2000 | Schima et al. | 600/16 |
| 6,250,880 B1 | * | 6/2001 | Woodard et al. | 415/182.1 |
| 6,503,450 B1 | * | 1/2003 | Afzal et al. | 422/45 |
| 6,689,315 B2 | * | 2/2004 | Linker et al. | 422/45 |
| 6,840,735 B2 | * | 1/2005 | Yaegashi et al. | 415/42 |

FOREIGN PATENT DOCUMENTS

| | | |
|---|---|---|
| DE | 41 23 433 A1 | 2/1992 |
| EP | 0 629 412 A2 | 12/1994 |
| EP | 0 629 412 A3 | 12/1994 |
| EP | 1 327 455 A2 | 7/2003 |
| WO | WO 00/64508 | 11/2000 |

* cited by examiner

*Primary Examiner*—Leslie R Deak
(74) *Attorney, Agent, or Firm*—Buchanan Ingersoll & Rooney PC

(57) ABSTRACT

A centrifugal blood pump apparatus has a centrifugal pump section including an impeller having a first magnetic material therein and rotating inside the housing to feed a fluid by a centrifugal force generated during a rotation thereof; an impeller rotational torque generation section having a rotor having a magnet for attracting the first magnetic material of the impeller thereto, and a motor for rotating the rotor; and a dynamic pressure groove formed at a portion, of an inner surface of the housing, located at a rotor-disposed side thereof. The centrifugal blood pump apparatus further includes an electromagnet for attracting the impeller in a direction opposite to a direction in which the magnet of the rotor attracts the impeller and helping the impeller levitate.

12 Claims, 18 Drawing Sheets

(A)

(B)

CENTRIFUGAL BLOOD PUMP APPARATUS

BACKGROUND OF THE PRESENT INVENTION

The present invention relates to a centrifugal blood pump apparatus for pumping a medical fluid, typically blood.

In recent medical treatment, centrifugal blood pumps are increasingly used in artificial heart/lung units for extracorporeal blood circulation. Centrifugal pumps of the magnetic levitation type wherein a driving torque from an external motor is transmitted to an impeller through magnetic coupling are commonly used because the physical communication between the blood chamber of the pump and the exterior can be completely excluded and invasion of bacteria can be prevented.

The present applicant proposed a centrifugal blood pump disclosed in U.S. Pat. No. 5,947,703.

The centrifugal blood pump includes the housing having the inlet port and the outlet port for blood and adapted to receive blood therein, and the impeller adapted to rotate within the housing for feeding blood by a centrifugal force developed during rotation, the uncontrolled magnetic bearing means (impeller rotational torque generation section) for magnetically supporting the impeller, and the controlled magnetic bearing means (impeller position control section) for magnetically supporting the impeller. The controlled magnetic bearing means and the uncontrolled magnetic bearing means cooperate such that the impeller rotates while it is held at a predetermined position within the housing. The impeller has a large number of hydrodynamic pressure grooves formed on its bottom surface (lower surface). Owing to the action of the hydrodynamic pressure groove, the impeller is attracted toward the impeller rotational torque generation section 3, when the impeller position control section is not operative (in other words, when the operation of electromagnet stops). However, at this time, the impeller rotates at a position spaced at a slight distance from the inner surface of the housing without contacting the inner surface thereof owing to the hydrodynamic bearing effect formed between the hydrodynamic pressure groove and the inner surface of the housing.

The above-described centrifugal blood pump apparatus is of a magnetic levitation type and has a favorable effect. The hydrodynamic pressure groove of the centrifugal blood pump apparatus acts when the impeller position control is stopped, i.e., when the operation of the electromagnet attracting the impeller thereto is stopped because of failure of the controlled magnetic bearing means (impeller position control section) for the control of the impeller. That is, the hydrodynamic pressure groove is not utilized in a normal rotation of the impeller. During the rotation of the impeller made only by the action of the hydrodynamic pressure groove, there is a fear that hemolysis occurs when the impeller has a small number of rotations. Since the impeller is levitated by a magnetic force, it is necessary to provide the centrifugal blood pump apparatus with an impeller position sensor. Thus it is very difficult to make the centrifugal blood pump apparatus compact. Further an electric power for the magnetic levitation of the impeller is required.

Therefore it is an object of the present invention to provide a centrifugal blood pump apparatus not of a magnetic levitation type but of a type in which the impeller is rotated without contacting a housing by utilizing the action of a hydrodynamic pressure groove. This construction eliminates the need for the use of a position sensor. Thereby it is possible to make the centrifugal blood pump apparatus compact. Further it is possible to secure a predetermined distance between the housing and the impeller and thereby reduce generation of hemolysis.

SUMMARY OF THE PRESENT INVENTION

In accordance with the present invention, the objects described above are achieved by a centrifugal blood pump apparatus that comprises a housing having a fluid inlet port and a fluid outlet port; a centrifugal pump section including an impeller having a first magnetic material therein and rotating inside said housing to feed a fluid by a centrifugal force generated during a rotation thereof; an impeller rotational torque generation section for attracting and rotating said impeller; and a hydrodynamic pressure groove formed at a portion of an inner surface of said housing at a rotor-disposed side or at a portion of a surface of said impeller at said rotor-disposed side, said impeller rotating without contacting said housing owing to an action of said hydrodynamic groove, said centrifugal blood pump apparatus further comprising an electromagnet for attracting said first magnetic material of said impeller or a second magnetic material provided on said impeller separately from said first magnetic material in a direction opposite to a direction in which said impeller rotational torque generation section attracts said first magnetic material and helping said impeller levitate.

BRIEF DESCRIPTION OF THE DRAWINGS

The above and other objects; features and advantages of the present invention will be better understood by reading the following description, taken in conjunction with the accompanying drawings.

DETAILED DESCRIPTION OF THE PREFERRED EMBODIMENTS

Figure 1:
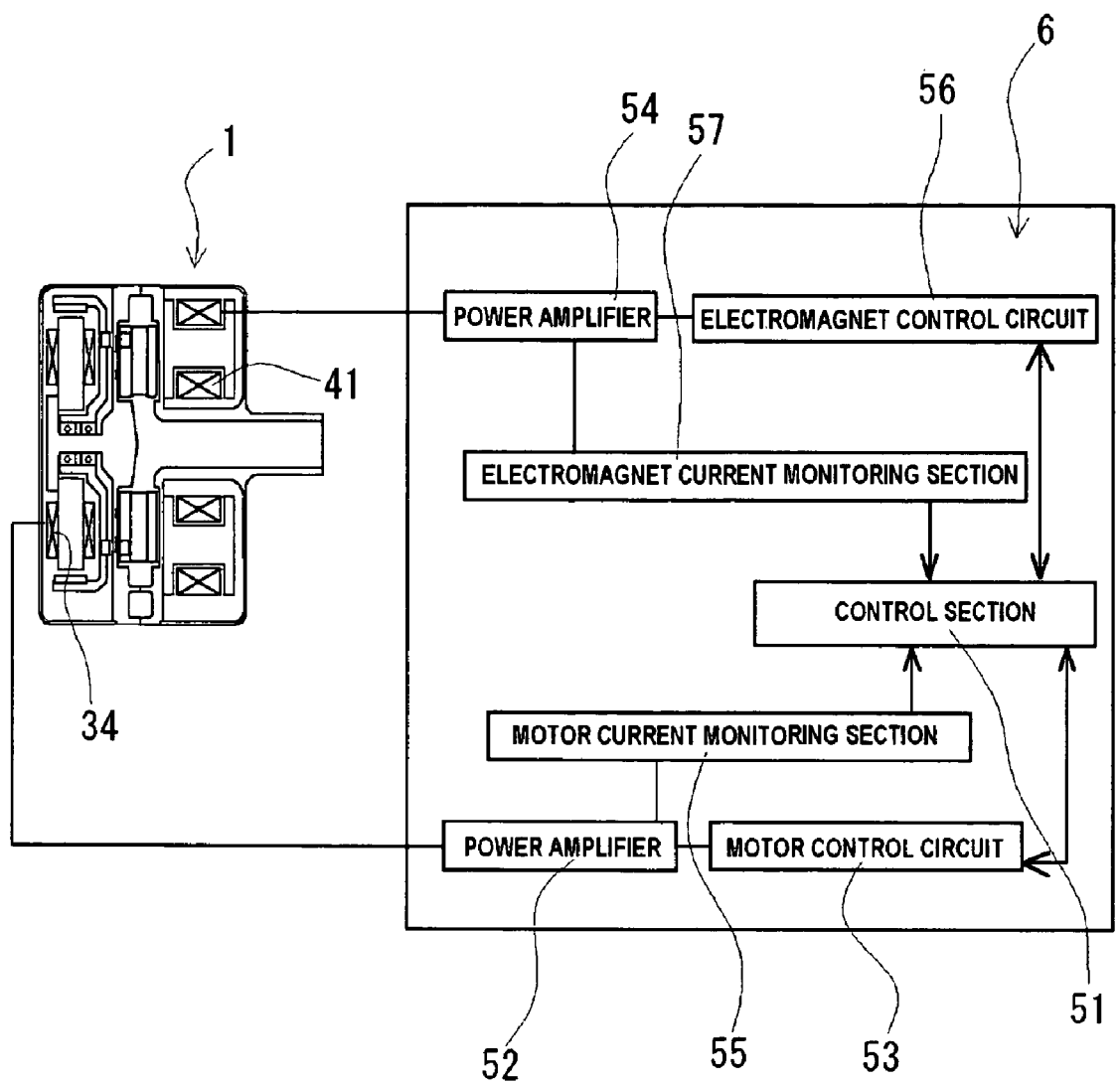
FIG. 1 is a block diagram showing a centrifugal blood pump apparatus, including a control mechanism, according to an embodiment of the present invention.

An embodiment of the centrifugal blood pump apparatus according to the present invention is described below with reference to FIGS. 1 through 11.

A centrifugal blood pump apparatus 1 of the present invention has a housing 20 having a fluid inlet port 22 and a fluid outlet port 23, a centrifugal pump section 2 including an impeller 21 having a first magnetic material 25 therein and rotating inside the housing 20 to feed a fluid by a centrifugal force generated during a rotation thereof, an impeller rotational torque generation section 3 for attracting and rotating said impeller, and a hydrodynamic pressure groove 38 formed at a portion of an inner surface of the housing 20 at a rotor-disposed side or at a portion of a surface of the impeller 21 at the rotor-disposed side. The impeller 21 rotates without contacting the housing 20 owing to an action of the hydrodynamic groove 38. The centrifugal blood pump apparatus 1 further includes an electromagnet 41 for attracting the first magnetic material 25 of the impeller 21 or a second magnetic material 28 provided on the impeller 21 separately from the first magnetic material 25 in a direction opposite to a direction in which the magnet 33 of the impeller rotational torque generation section 3 (in this embodiment, rotor 31) attracts the first magnetic material 25 and helping the impeller 21 levitate.

In this embodiment, the impeller rotational torque generation section 3 has rotor 31 having a magnet 33 for attracting the first magnetic material 25 of the impeller 21 of the centrifugal blood pump section 2 and a motor 34 for rotating the rotor 31.

In the centrifugal blood pump apparatus 1, the impeller is levitated not by a magnetic force, but rotated owing to a hydrodynamic pressure generated by the hydrodynamic pressure groove without contacting the housing. This mechanism elinmnates the need for the installation of a position sensor for the impeller, thus making the centrifugal blood pump apparatus compact. Since the centrifugal blood pump apparatus has the electromagnet 41 for assisting the levitation of the impeller 21, it is possible to secure a predetermined distance between the housing accommodating the hydrodynamic pressure groove and the impeller and reduce generation of hemolysis. Since the electromagnet serves as the means for merely assisting the levitation of the impeller, the electromagnet consumes a small amount of electric power.

Figure 2:
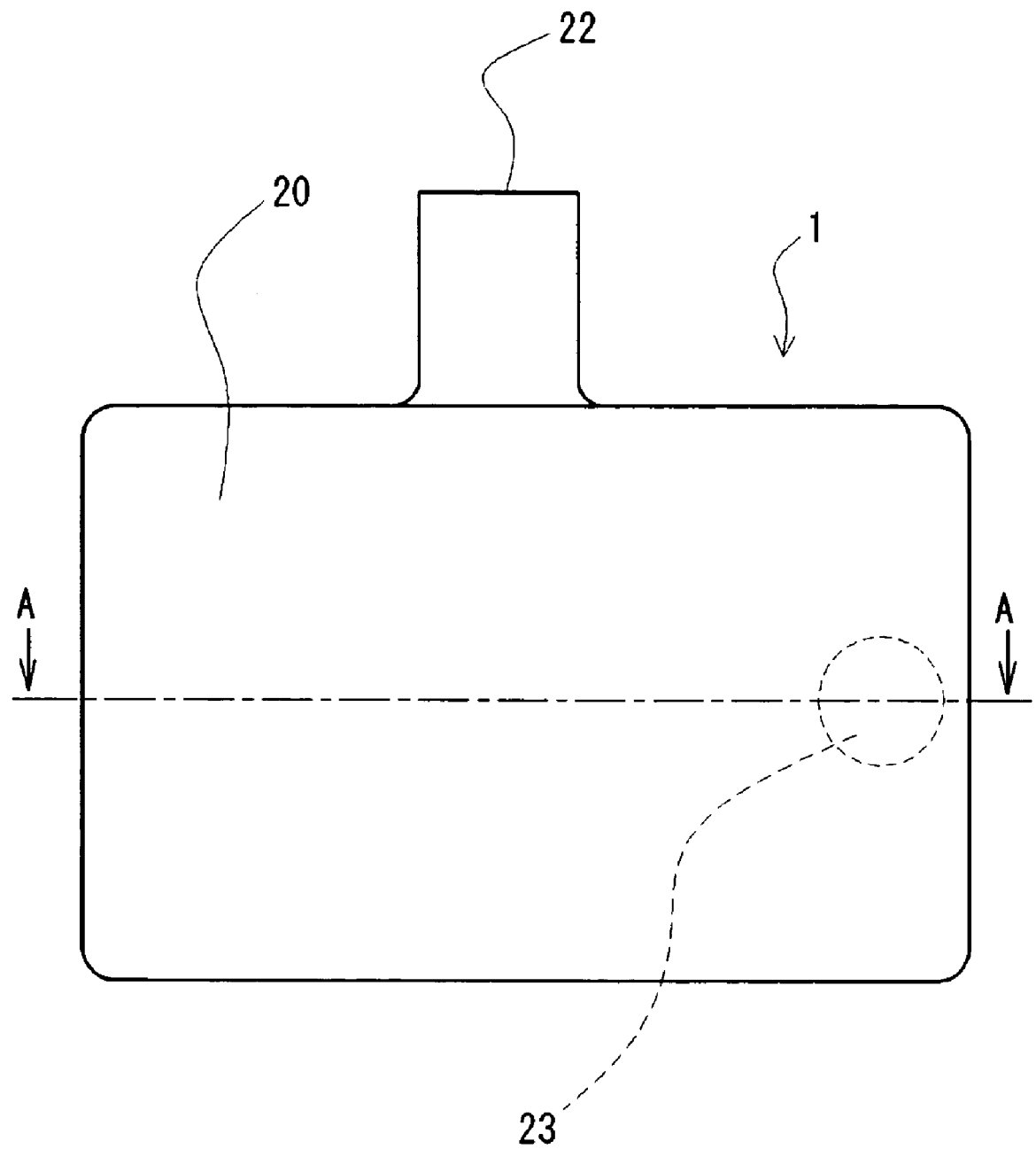
FIG. 2 is a front view showing an example of the centrifugal blood pump apparatus of the present invention.
Figure 6:
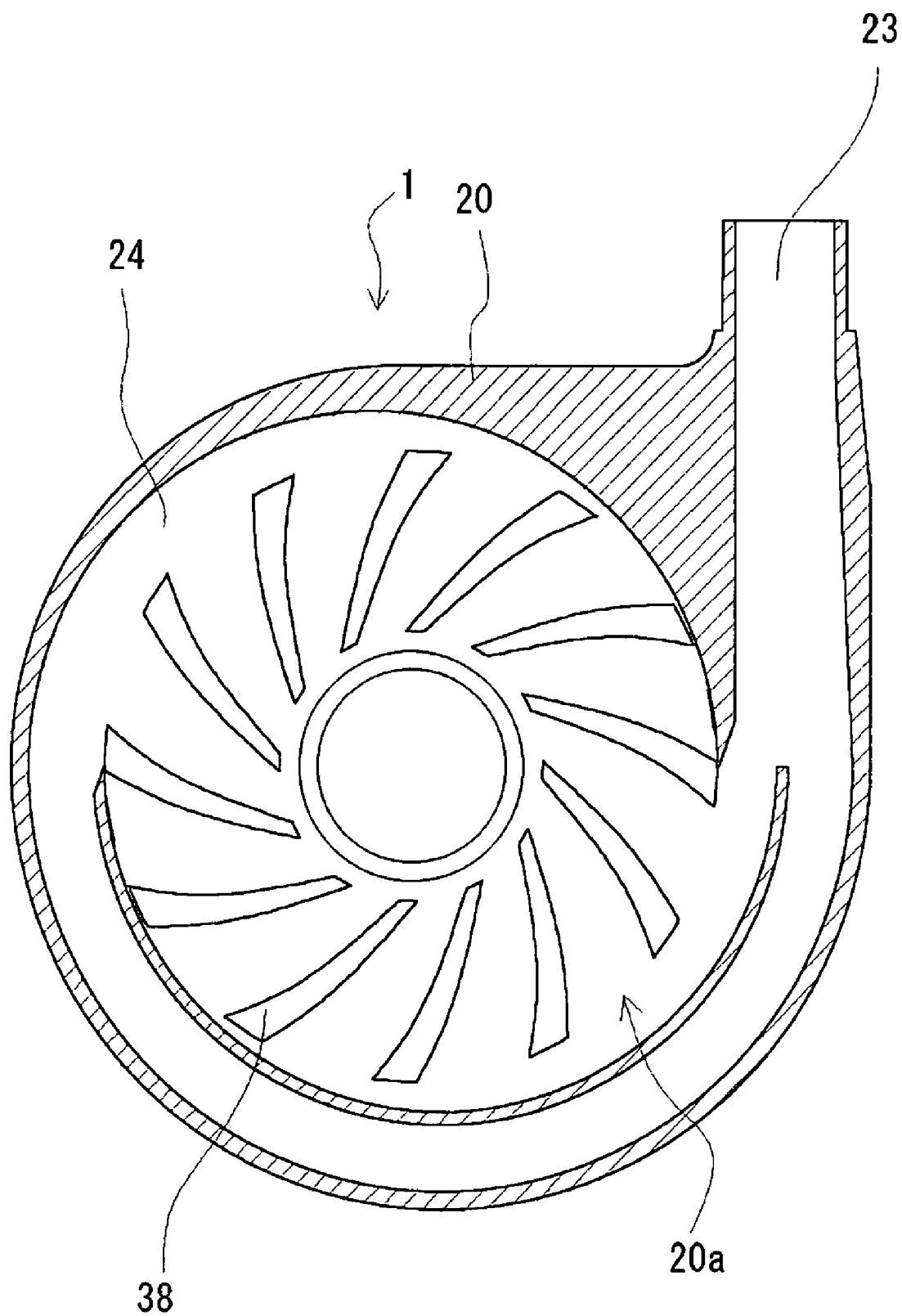
FIG. 6 is a sectional view showing a state in which an impeller is removed from the sectional view, taken along the line A-A of FIG. 2, showing the centrifugal blood pump apparatus.

As shown in FIGS. 2 and 6, the centrifugal blood pump apparatus 1 of the embodiment has the housing 20 having the blood inlet port 22 and the blood outlet port 23, the centrifugal pump section 2 having the impeller 21 rotating inside the housing 20 to feed blood by a centrifugal force generated during its rotation, the impeller rotational torque generation section 3 for the impeller 21, and an assistant impeller attraction section 4 for the impeller 21.

Figure 4:
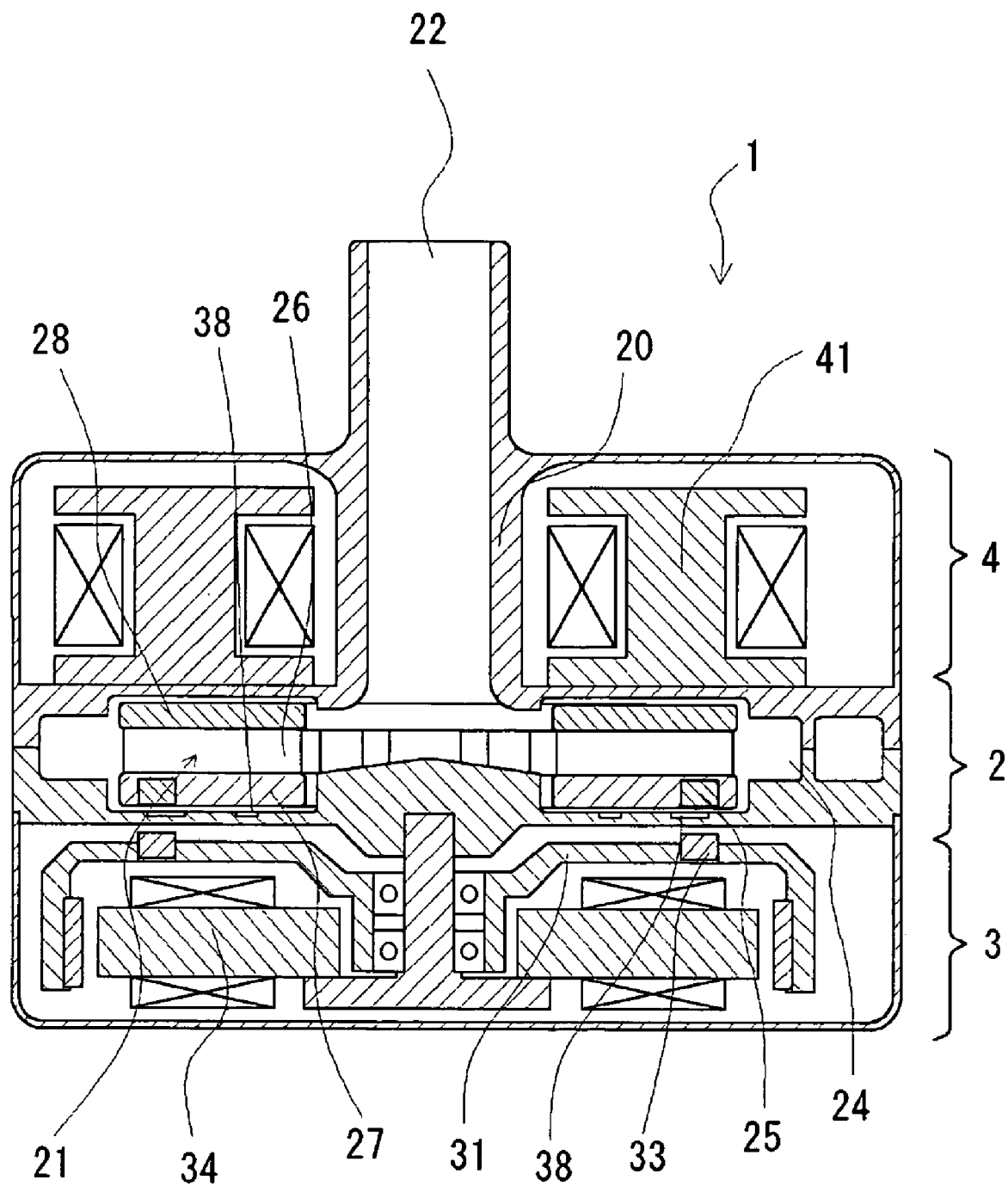
FIG. 4 is a vertical sectional view showing the centrifugal blood pump apparatus of the embodiment shown in FIG. 2.

As shown in FIG. 4, the impeller 21 rotates without contacting the inner surface of the housing 20 owing to the hydrodynamic pressure generated by the hydrodynamic pressure groove while the impeller 21 is rotating. In the centrifugal blood pump apparatus 1, the electromagnet 41 attracts the impeller 21 in the direction opposite to the direction in which the rotor 31 attracts the impeller 21. Therefore the impeller 21 rotates with the impeller 21 spaced at a longer distance from the housing than a housing-to-impeller distance provided by the action of a conventional hydrodynamic pressure groove.

Figure 3:
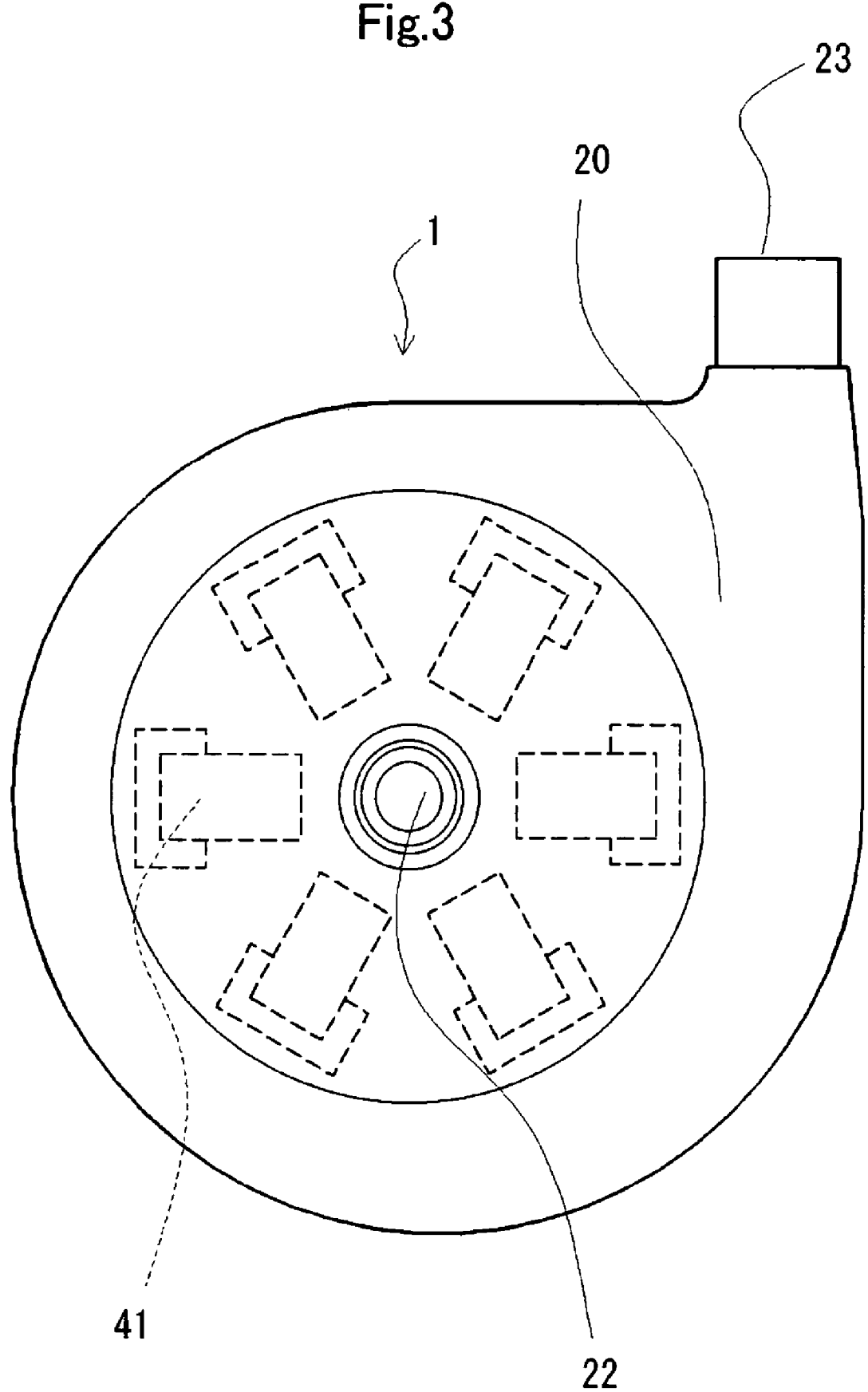
FIG. 3 is a plan view showing the centrifugal blood pump apparatus shown in FIG. 2.
Figure 5:
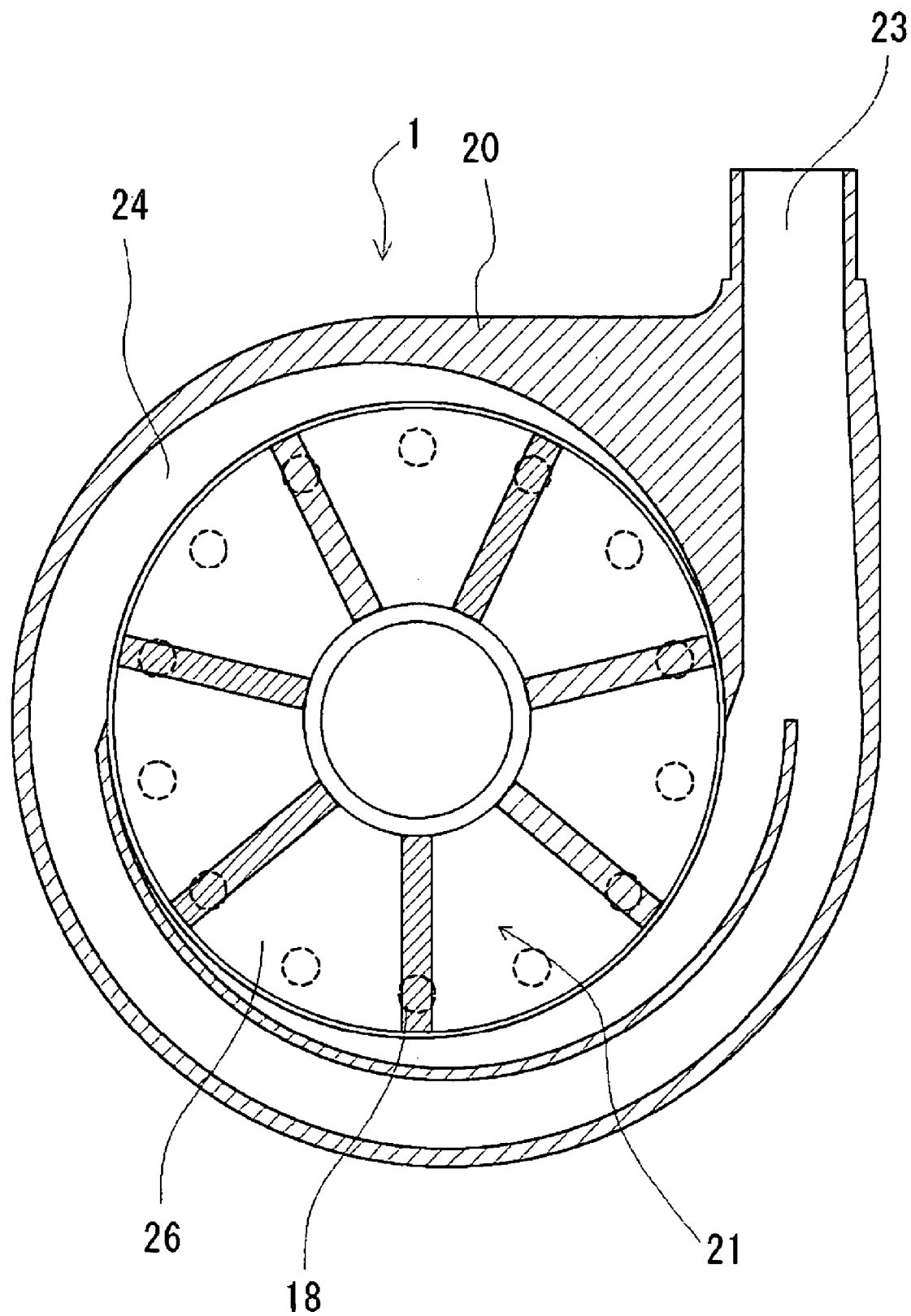
FIG. 5 is a sectional view, taken along a line A-A of FIG. 2, showing the centrifugal blood pump apparatus.

The housing 20 has the blood inlet port 22 and the blood outlet port 23. The housing 20 is made of a nonmagnetic material. The housing 20 accommodates a blood chamber 24 communicating with the blood inlet port 22 and the blood outlet port 23. The housing 20 also accommodates the impeller 21 therein. The blood inlet port 22 projects substantially vertically from the vicinity of the center of the upper surface of the housing 20. As shown in FIGS. 3 and 5, the blood outlet port 23 projects tangentially from a side surface of the approximately cylindrical housing 20.

As shown in FIG. 5, the disc-shaped impeller 21 having a through-hole in the center thereof is accommodated inside the blood chamber 24 formed inside the housing 20. As shown in FIG. 4, the impeller 21 includes an annular plate-shaped member (lower shroud) 27 forming the lower surface thereof, an annular plate-shaped member (upper shroud) 28 which forms the upper surface thereof and is open at the center thereof, and a plurality of vanes (seven) 18 formed between the lower shroud 27 and the upper shroud 28. A plurality of (seven) blood passages 26 partitioned from one another by adjacent vanes 18 is formed between the lower shroud 27 and the upper shroud 28. As shown in FIG. 5, each of the blood passages 26 communicates with the center opening of the impeller 21 and extends from the center opening of the impeller 21 to its periphery, with each of the blood passages 26 becoming gradually larger in the width thereof. In other words, the vanes 18 are formed between the adjacent blood passages 26. In the embodiment, the vanes 18 and blood passages 26 are spaced at equiangular intervals respectively and formed in substantially the same shape respectively.

As shown in FIG. 4, a plurality (for example, 14 to 24) of the first magnetic materials 25 (permanent magnet, follower magnet) are embedded in the impeller 21. In this embodiment, the first magnetic materials 25 are embedded in the lower shroud 27. The first magnetic materials (permanent magnet) 25 are provided so that the permanent magnet 33 provided in the rotor 31 of the impeller rotational torque generation section 3 to be described later attracts the impeller 21 toward the side opposite to the side where the blood inlet port 22 is disposed. That is, the first magnetic materials 25 serve as a means for magnetically coupling the impeller 21 and the rotor 31 to each other and transmitting the rotational torque from the impeller rotational torque generation section 3 to the impeller 21.

The magnetic coupling between the impeller 21 and the rotor 31 is ensured by embedding a plurality of the first magnetic materials 25 in the impeller 21, as will be described later. It is preferable that each of the first magnetic materials (permanent magnet) 25 are circular. Alternatively, it is possible to use a plurality ring-shaped magnet having multi-poles (for example, 24 poles). In other words, the first magnetic materials (permanent magnet) 25 may consist of a plurality of small magnets having positive poles and negative poles alternately arranged in the shape of a ring or small magnets having the same polarity arranged in the shape of a ring.

The impeller 21 further includes the second magnetic member 28 which itself constitutes the upper shroud or which is provided inside the upper shroud. In the embodiment, the entire upper shroud is formed of the second magnetic member 28. The second magnetic member 28 is provided so that the electromagnet 41 attracts the impeller 21 to the side opposite to the rotor-disposed side, namely, toward the blood inlet port 22. The second magnetic member 28 is made of magnetic stainless steel.

The impeller 21 is attracted toward the rotor-disposed side and at the same time, toward the side opposite to the rotor-disposed side by the electromagnet 41. Therefore the impeller 21 disposed inside the housing 20 rotates inside the housing 20 with the impeller 21 out of contact with the housing 20 and with the impeller 21 spaced at the longer distance from the housing than the housing-to-impeller distance provided by the action of the conventional hydrodynamic pressure groove.

As shown in FIG. 4, the impeller rotational torque generation section 3 includes the rotor 31 accommodated in the housing 20 and the motor 34, for rotating the rotor 31, also accommodated in the housing 20. The rotor 31 has a plurality of the permanent magnets 33 disposed on a surface thereof adjacent to the blood pump section 2. The center of the rotor 31 is fixedly secured to the rotational shaft of the motor 34. A plurality of the permanent magnets 33 are equiangularly distributed in accordance with the arrangement mode (number and position) of the permanent magnets 25 of the impeller 21.

It is preferable to dispose the permanent magnets 25 in such a way that an attractive force is generated between the impeller 21 and the motor 34, even though the coupling therebetween performed by the permanent magnets 25 fails owing to application of an external force to the centrifugal blood pump apparatus. Thereby the coupling between the impeller 21 and the motor 34 returns to a normal state easily.

Figure 8:
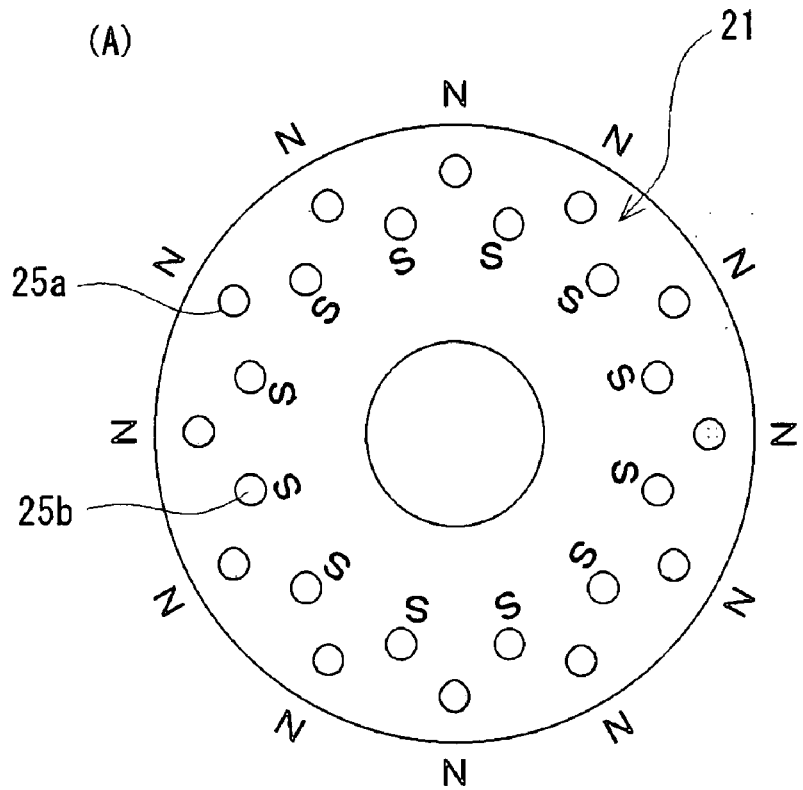
FIG. 8 is an explanatory view for explaining a mode of magnetic coupling between the impeller and a rotor of the centrifugal blood pump apparatus of the present invention.
Figure 8:
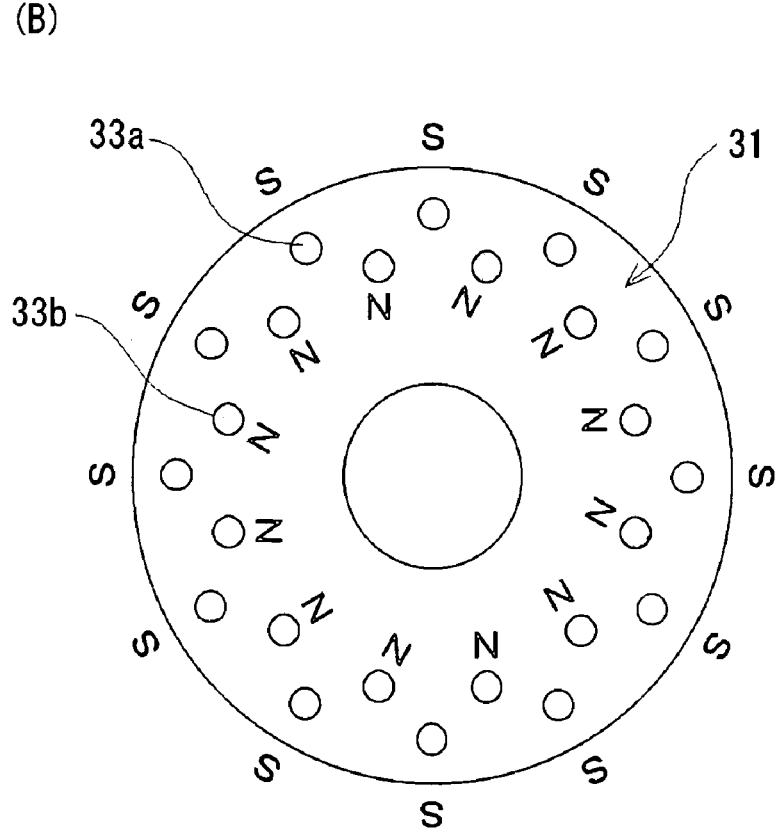

As shown in FIG. 8, the first magnetic materials of the impeller 21 and the magnets of the rotor 31 for attracting the first magnetic materials consist of permanent magnets 25, 33 respectively. The permanent magnets 25, 33 are arranged on a circumference respectively in such a way that the permanent magnets 25 and 33 have the same polarity respectively. The permanent magnets 25 of the impeller 21 and the permanent magnets 33 of the rotor 31 may be arranged on two different circumferences facing each other in such a way that the polarity of the entire permanent magnets 25 arranged on one circumference and that of the entire permanent magnets 33 arranged on the other circumference are opposite to each other. That is, the permanent magnets 25 of the impeller 21 and the permanent magnets 33 of the rotor 31 may be arranged on a circumference in the impeller 21 and on a circumference in the rotor 31 respectively in such a way that the polarity of the permanent magnets 25 and that of the permanent magnets 33 are opposite to each other and that the permanent magnets 25 arranged on the circumference in the impeller 21 and the permanent magnets 33 arranged on the circumference in the rotor 31 have the same polarity respectively.

As an example of the arrangement of the permanent magnets, as shown in FIG. 8, a plurality of the permanent magnets 25a having the same polarity (for example, north pole) is arranged on a circumference in the impeller 21. In correspondence to the disposition of the permanent magnets 25a of the impeller 21, a plurality of the permanent magnets 33a having the same polarity (for example, south pole) which is reverse to that of the permanent magnets 25a is arranged on a circumference having the same diameter as that of the circumference in the impeller 21. It is preferable that a plurality of the permanent magnets 25a is arranged at equiangular intervals around the axis of the impeller 21. It is preferable that a plurality of the permanent magnets 33a is arranged at equiangular intervals around the axis of the rotor 31. It is preferable that the central angle of the permanent magnets 25a is set equally to that of the permanent magnets 33a or set to integral multiples of that of the permanent magnets 33a or vice versa.

As shown in FIG. 8 it is preferable that in the impeller 21, a plurality of permanent magnets 25b having the same polarity (south pole) which is opposite to the polarity (north pole) of the permanent magnets. 25a is arranged on a circumference inward from the circumference on which the permanent magnets 25b are arranged. It is preferable that in the rotor 31, in correspondence to the disposition of the permanent magnets 25b of the impeller 21, a plurality of permanent magnets 33b having the same polarity (north pole) opposite to the polarity (south pole) of the permanent magnets 25b are arranged on a circumference having the same diameter as that of the circumference on which the permanent magnets 25b are arranged. It is preferable that a plurality of the permanent magnets 25b is arranged at equiangular intervals around the axis of the impeller 21. It is preferable that a plurality of the permanent magnets 33b is arranged at equiangular intervals around the axis of the rotor 31. It is preferable that the central angle of the permanent magnets 25b is set equally to that of the permanent magnets 33b or set to integral multiples of that of the permanent magnets 33b or vice versa.

As shown in FIGS. 3 and 4, the assistant impeller attraction section 4 has at least one stationary electromagnet 41 for attracting the second magnetic member 28 of the impeller 21 thereto. More specifically, the assistant impeller attraction section 4 has a plurality of the electromagnets 41 accommodated in the housing 20. The electromagnets 41 are spaced at equiangular intervals. Each of the electromagnets 41 consists of a core and a coil. The assistant impeller attraction section 4 has six electromagnets 41 in this embodiment. It is preferable that the assistant impeller attraction section 4 has one to eight electromagnets 41.

As shown in FIG. 6, in the centrifugal blood pump apparatus 1 of this embodiment, the housing 20 has an inner surface 20a accommodating the impeller 21 and forming the blood chamber 24. The housing 20 accommodates the hydrodynamic pressure groove 38 formed on a portion, of the inner surface 20a of the housing 20, disposed at the rotor-disposed side thereof. When the number of rotations of the impeller 21 becomes more than a predetermined number of rotations, a hydrodynamic bearing effect is generated between the hydrodynamic pressure groove 38 and the impeller 21. Thereby the impeller 21 rotates without contacting the inner surface of the housing 20.

As shown in FIG. 6, the hydrodynamic pressure groove 38 has a size corresponding to that of the bottom surface of the impeller 21 (side surface of rotor). In the centrifugal blood pump apparatus 1 of the embodiment, the hydrodynamic pressure groove 38 extends spirally (in other words, curved) outwardly to the vicinity of the outer edge of the inner surface 20a of the housing 20, with one end of the hydrodynamic pressure groove 38 disposed on the circumference of a circle spaced outward at a short distance from the center of the inner surface 20a of the housing 20 and with the width thereof becoming gradually outwardly larger. A plurality of the hydrodynamic pressure grooves 38 has substantially the same configuration. The hydrodynamic pressure grooves 38 are spaced at almost equal intervals. Each of the hydrodynamic pressure grooves 38 is concavely formed. It is preferable that the depth of the hydrodynamic pressure groove 38 is in the range of 0.005 to 0.4 mm. It is also preferable that the number of the hydrodynamic pressure grooves 38 is in the range of 6 to 36. In the embodiment, 12 hydrodynamic pressure grooves 38 are provided at equiangular intervals around the axis of the impeller 21.

The hydrodynamic pressure groove may be formed on the surface of the impeller 21 at the rotor-disposed side thereof instead of forming it at the housing side. In this case, it is preferable that the hydrodynamic pressure groove has the same construction as that of the hydrodynamic pressure groove 38 disposed on the inner surface of the housing 20 at the rotor-disposed side thereof.

Since the hydrodynamic pressure groove 38 has the above-described construction, the impeller 21 is attracted toward the impeller torque generation section 3. Owing to the hydrodynamic bearing effect generated between the hydrodynamic pressure groove 38 and the bottom surface of the impeller 21 (or between the dynamic pressure groove formed on the surface of the impeller 21 at the rotor-disposed side thereof and the inner surface of the housing), the impeller 21 rotates without contacting the inner surface of the housing 20, with the impeller 21 spaced at a slight interval from the inner surface of the housing 20. Thereby a blood passage can be secured between the bottom surface of the impeller 21 and the inner surface of the housing 20. Consequently it is possible to prevent blood from staying therebetween and thrombus from occurring because the blood does not stay therebetween. In addition, because the hydrodynamic pressure groove 38 displays a blood-stirring action between the bottom surface of the impeller 21 and the inner surface of the housing 20 in a normal state, it is possible to prevent blood from staying therebetween.

Figure 7:
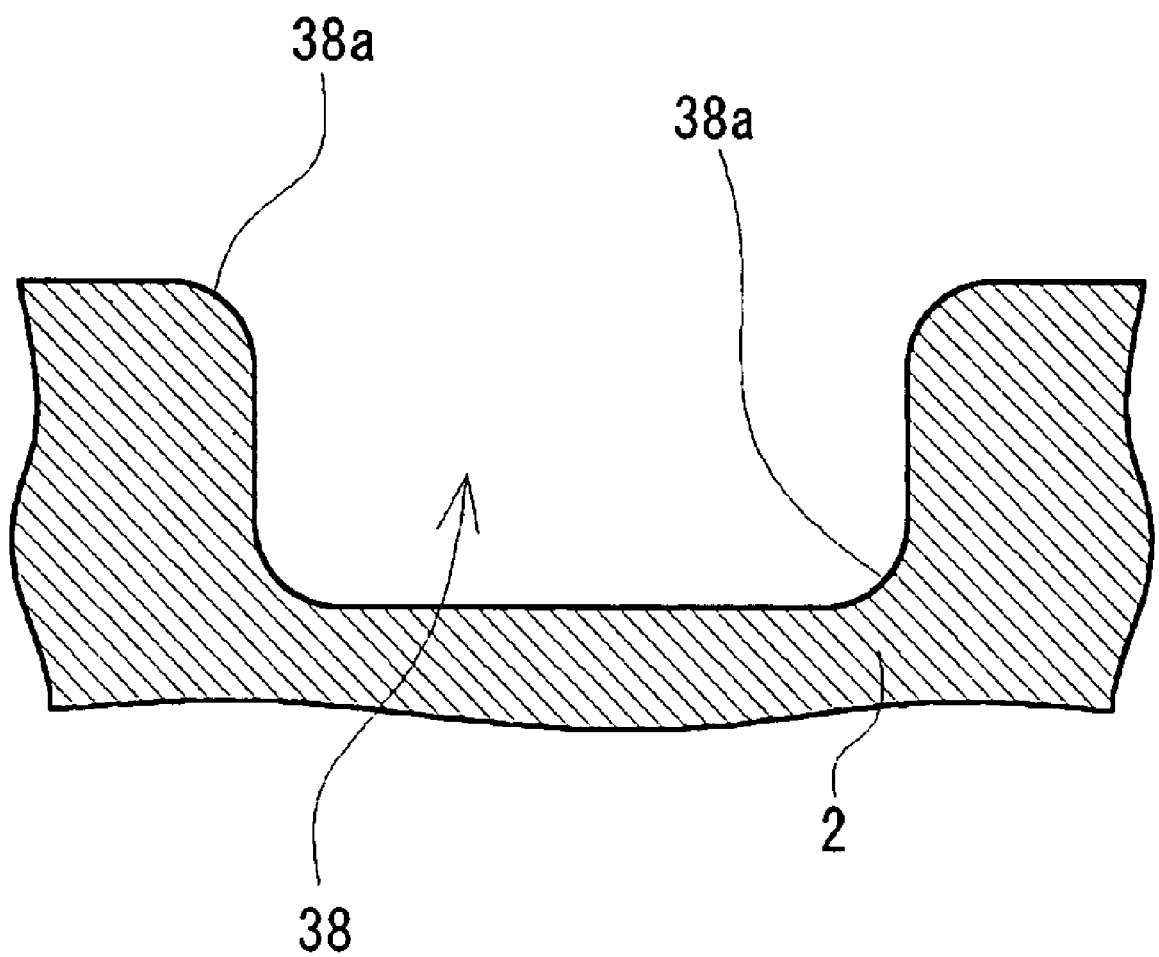
FIG. 7 is an explanatory view for explaining the configuration of a corner of a hydrodynamic pressure groove of the centrifugal blood pump apparatus of the present invention.

It is preferable that as shown in FIG. 7, a corner 38a of the hydrodynamic pressure groove 38 is chamfered to allow the corner 38a to have a radius of rounding at not less than 0.05 mm. Thereby it is possible to reduce generation of hemolysis.

Figure 17:
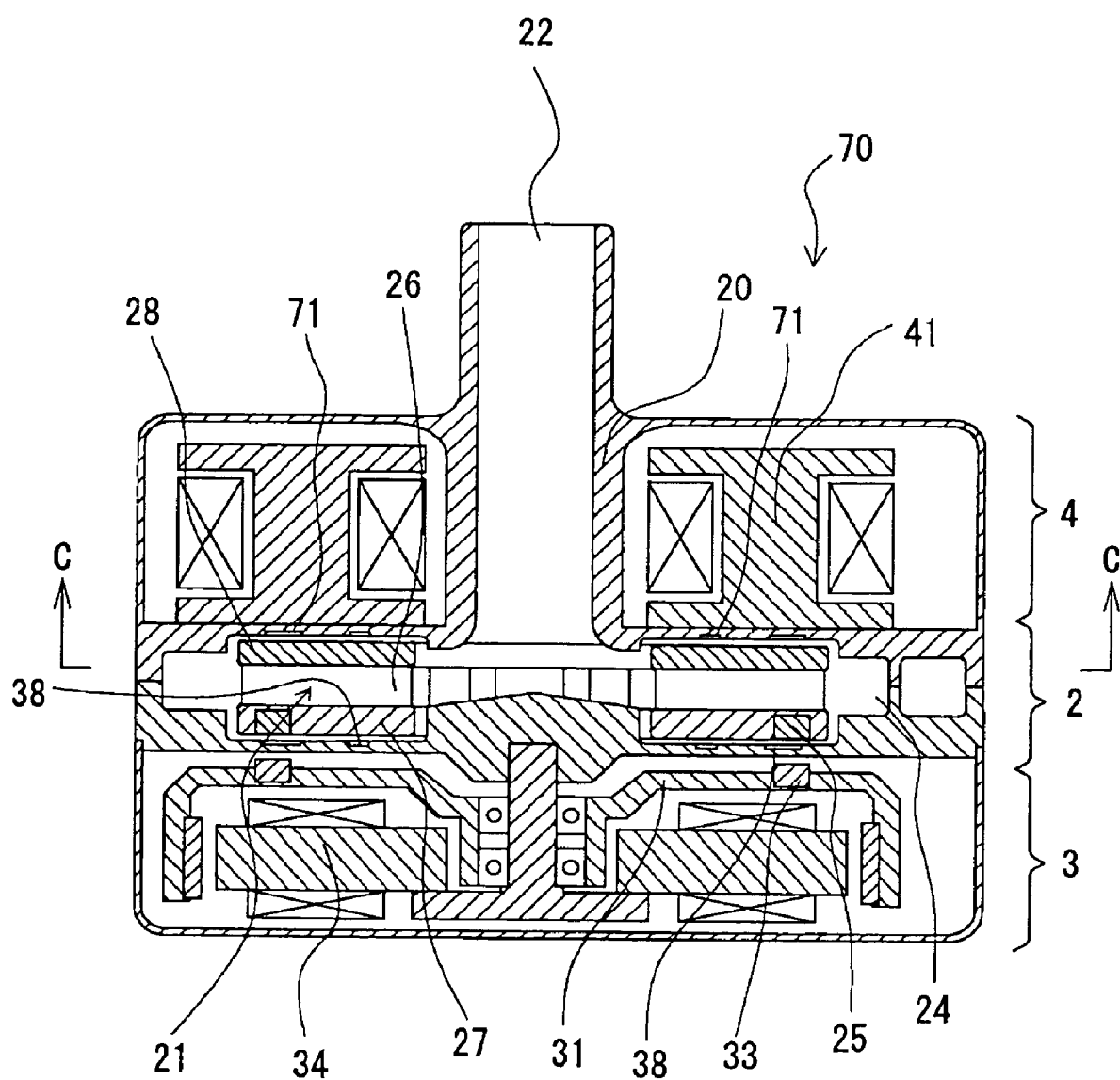
FIG. 17 is a sectional view showing another example of the centrifugal blood pump apparatus of the present invention.
Figure 18:
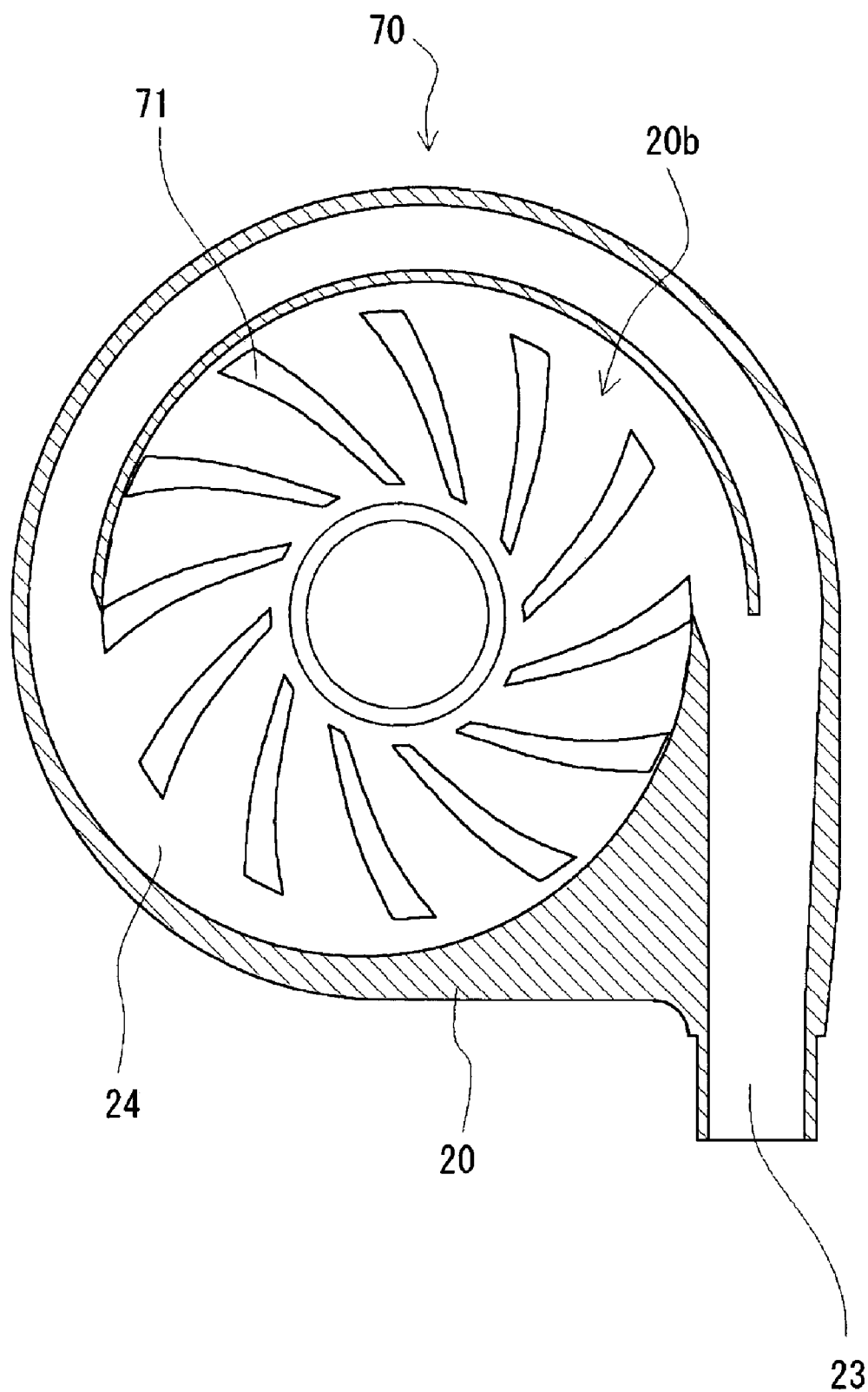
FIG. 18 is a sectional view showing a state in which an impeller is removed from the sectional view, taken along the line C-C in FIG. 17, showing the centrifugal blood pump apparatus.

In a centrifugal blood pump apparatus 70 shown in FIGS. 17 and 18, the housing 20 has an inner surface 20a accommodating the impeller 21 and forming the blood chamber 24. In addition to the hydrodynamic pressure groove 38 formed on a portion, of the inner surface 20a of the housing 20, disposed at the rotor-disposed side thereof, the housing 20 has a second hydrodynamic pressure groove 71 formed on a portion, of an inner surface 20b of the housing 20, disposed at the electromagnet-disposed side thereof. When the number of rotations of the impeller 21 becomes more than a predetermined number of rotations, a hydrodynamic bearing effect is generated between the hydrodynamic pressure groove 38 and the impeller 21. Thereby the impeller 21 rotates without contacting the inner surface 20a of the housing 20 and is prevented from closely contacting the inner surface 20b of the housing 20, when the centrifugal blood pump apparatus 70 is subjected to an external impact and when an excessive hydrodynamic pressure is generated by the hydrodynamic pressure groove 38.

Similarly to the above-described hydrodynamic pressure groove 38, the hydrodynamic pressure groove 71 has a size corresponding to that of the upper surface of the impeller 21 (side surface of electromagnet). In the centrifugal blood pump apparatus 70 of this embodiment, the hydrodynamic pressure groove 38 extends spirally (in other words, curved) outwardly to the vicinity of the outer edge of the inner surface 20b of the housing 20, with one end of the hydrodynamnic pressure groove 71 disposed on the circumference of a circle spaced outward at a short distance from the center of the inner surface 20a of the housing 20 and with the width thereof becoming gradually outwardly larger. A plurality of the hydrodynamic pressure grooves 71 has substantially the same configuration. The hydrodynamic pressure grooves 71 are spaced at almost equal intervals. Each of the hydrodynamic pressure grooves 71 is concavely formed. It is preferable that the depth thereof is in the range of 0.005 to 0.4 mm. It is also preferable that the number of the hydrodynamic pressure grooves 71 is in the range of 6 to 36. In the embodiment, 12 hydrodynamic pressure grooves 38 are provided at equiangular intervals around the axis of the impeller 21.

The second hydrodynamic pressure groove may be formed at a portion, of the surface of the impeller 21, at the electromagnet-disposed side thereof instead of forming it at the housing side. In this case, it is preferable that the second hydrodynamic pressure groove has the same construction as that of the hydrodynamic pressure groove 71 formed on the inner surface of the housing 20 at the rotor-disposed side thereof. It is preferable that similarly to the hydrodynamic pressure groove shown in FIG. 7, a corner of the hydrodynamic pressure groove 71 is chamfered to allow the corner to have a radius of rounding at not less than 0.05 mm. Thereby it is possible to reduce generation of hemolysis.

It is preferable that the second hydrodynamic pressure groove 71 is formed on a portion of an inner surface 20b of the housing 20. Because, the second hydrodynamic pressure groove 71 is able to be formed easily and the impeller can be made thinly and lightly even more in the case that the second hydrodynamic pressure groove 71 is formed to the impeller.

A centrifugal blood pump apparatus according to another embodiment of the present invention will be described below.

Figure 9:
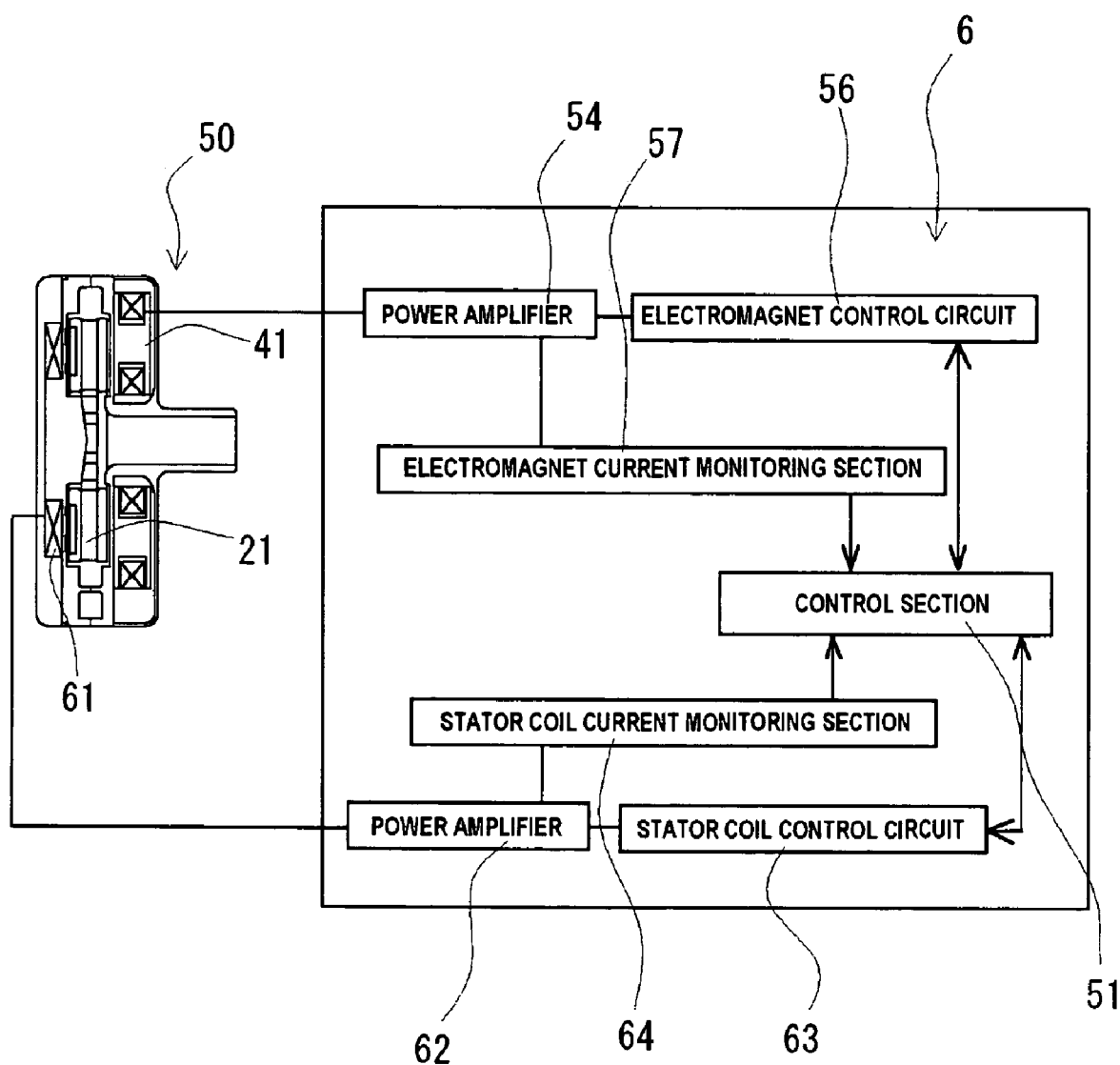
FIG. 9 is a block diagram showing a centrifugal blood pump apparatus, including a control mechanism, according to another embodiment of the present invention.
Figure 10:
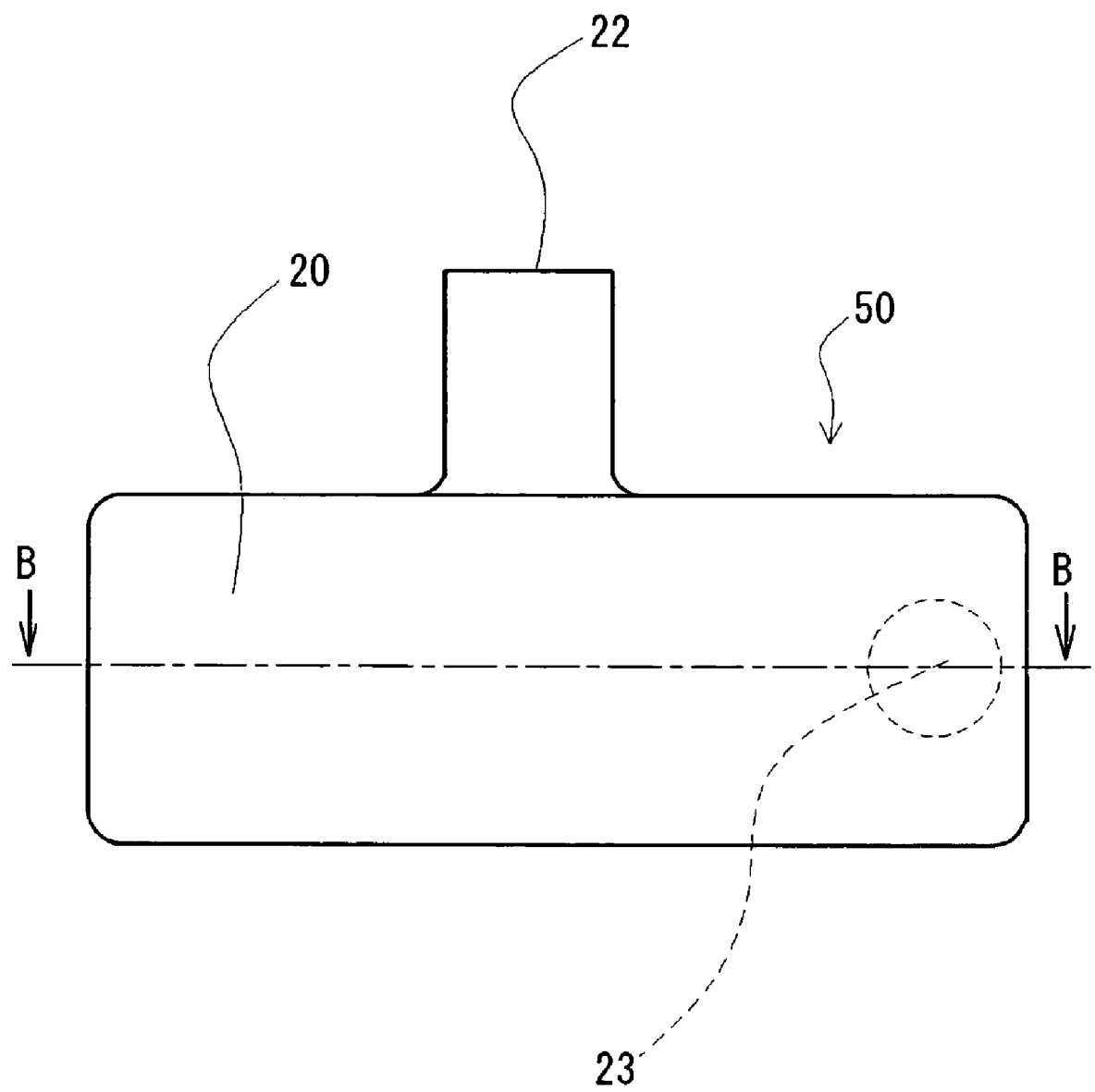
FIG. 10 is a front view showing an example of the centrifugal blood pump apparatus of the present invention.
Figure 11:
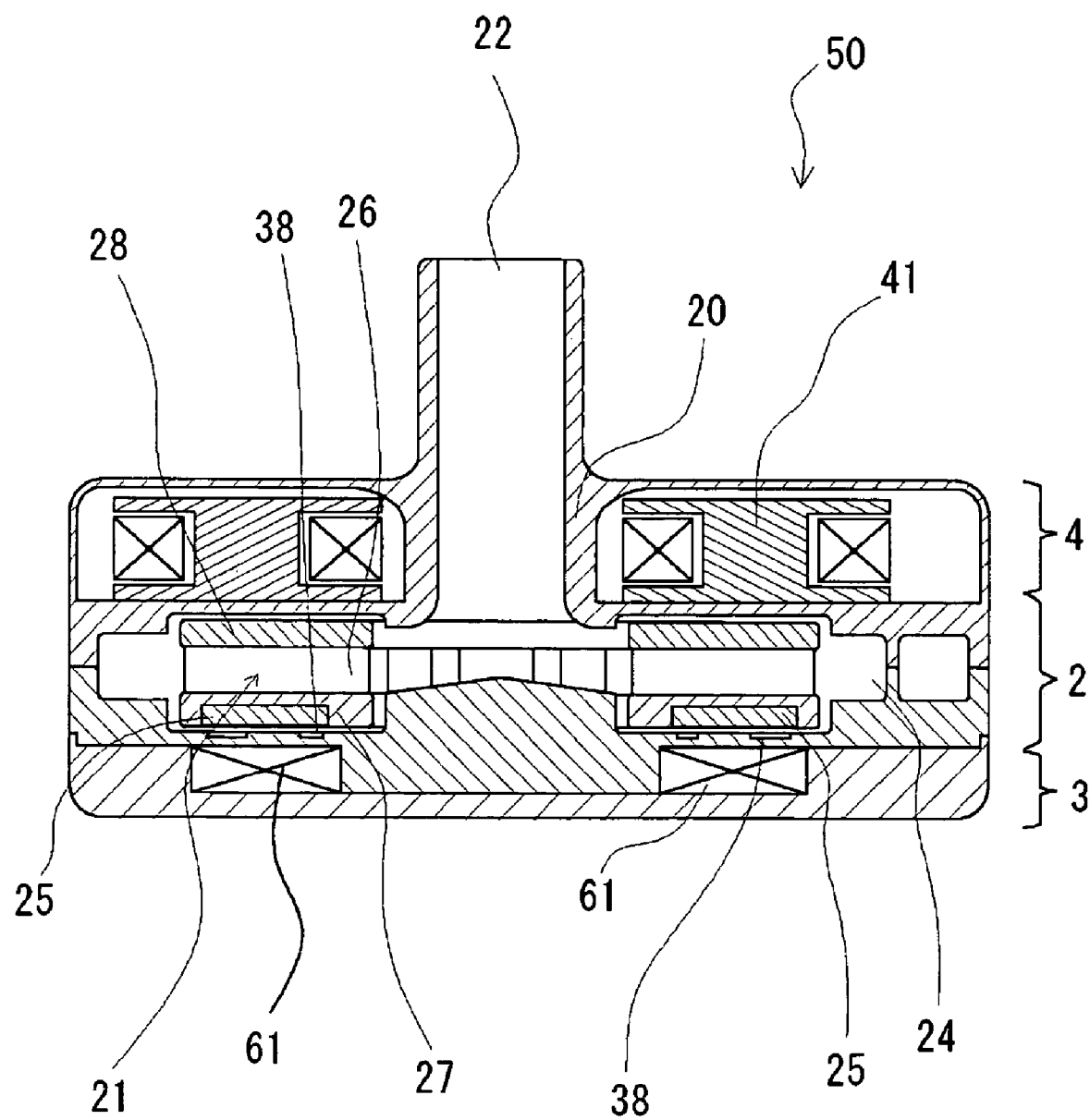
FIG. 11 is a vertical sectional view showing the centrifugal blood pump apparatus of the embodiment shown in FIG. 10.
Figure 12:
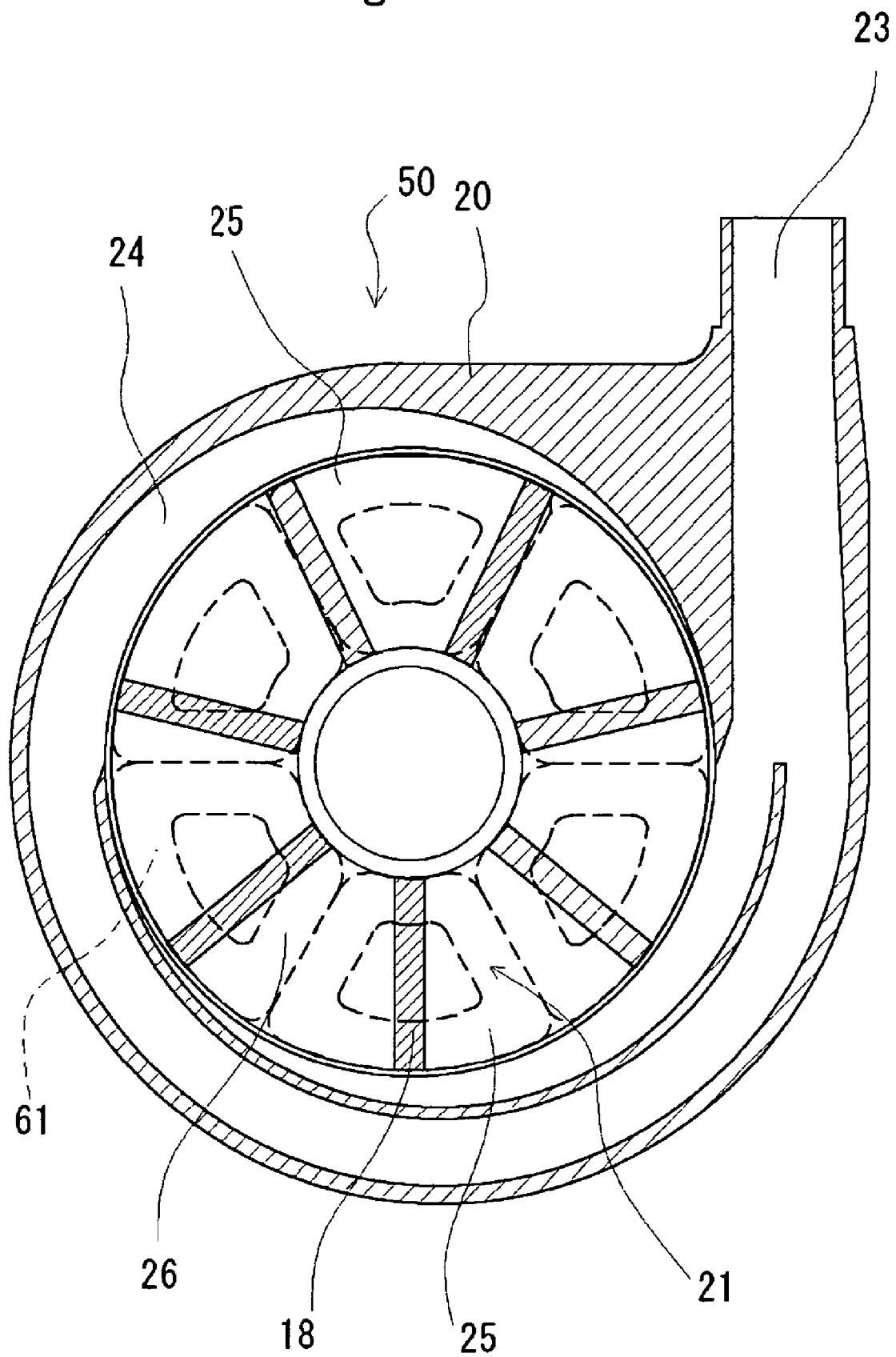
FIG. 12 is a sectional view, taken along a line B-B in FIG. 10, showing the centrifugal blood pump apparatus.
Figure 13:
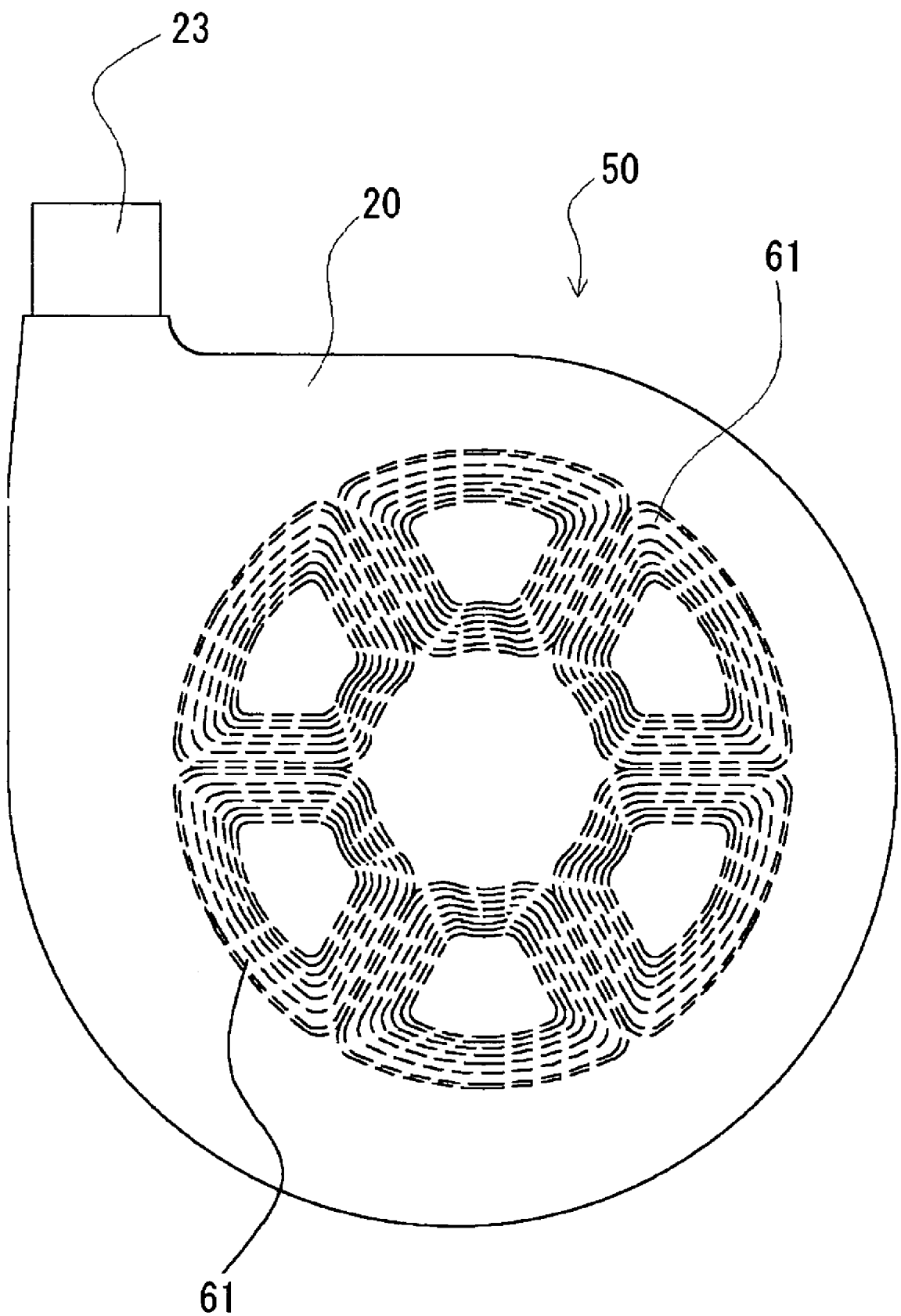
FIG. 13 is a bottom view showing the centrifugal blood pump apparatus shown in FIG. 10.

FIG. 9 is a block diagram showing: a centrifugal blood pump apparatus, including a control mechanism, according to another embodiment of the present invention. FIG. 10 is a front view showing an example of the centrifugal blood pump apparatus of the present invention. FIG. 11 is a vertical sectional view showing the centrifugal blood pump apparatus of the embodiment shown in FIG. 10. FIG. 12 is a sectional view, taken along a line B-B in FIG. 10, showing the centrifugal blood pump apparatus. FIG. 13 is a bottom view showing the centrifugal blood pump apparatus shown in FIG. 10. The plan view of the centrifugal blood pump apparatus shown in FIG. 10 is the same as that shown in FIG. 3. A section obtained by removing an impeller from the sectional view, taken along the line B-B of FIG. 10, showing the centrifugal blood pump apparatus is the same as that shown in FIG. 6. Thus regarding them, FIGS. 3 and 6 are referred to.

A centrifugal blood pump apparatus 50 of the present invention has a housing 20 having a fluid inlet port 22 and a fluid outlet port 23, a centrifugal pump section 2 including an impeller 21 having a first magnetic material 25 therein and rotating inside the housing 20 to feed a fluid by a centrifugal force generated during a rotation thereof, an impeller rotational torque generation section 3 for attracting and rotating the impeller that has a plurality of stator coils 61, disposed circumferentially to rotate the impeller 21, for attracting the first magnetic material 25 of the impeller 21 of the centrifugal blood pump section 2, and a hydrodynamic pressure groove 38 formed at a portion of an inner surface of the housing 20 at a stator coil-disposed side or at a portion of a surface of the impeller 21 at the stator coil-disposed side thereof. The impeller 21 rotates without contacting the housing 20 owing to an action of the hydrodynamic groove 38. The centrifugal blood pump apparatus 50 further includes an electromagnet 41 for attracting the first magnetic material 25 of the impeller 21 or a second magnetic material 28 provided on the impeller 21 separately from the first magnetic material 25 in a direction opposite to a direction in which the stator coils 61 attract the first magnetic material 25 and helping the impeller 21 levitate.

As shown in FIG. 11, the centrifugal blood pump apparatus 50 of this embodiment has the housing 20 having the blood inlet port 22 and the blood outlet port 23, the centrifugal pump section 2 including the impeller 21 rotating inside the housing 20 to feed blood by a centrifugal force generated during its rotation, the impeller rotational torque generation section 3 for the impeller 21, and an assistant impeller attraction section 4 for the impeller 21.

The centrifugal blood pump apparatus 50 of this embodiment is similar to the centrifugal blood pump apparatus 1 in the construction except the construction of the impeller rotational torque generation section 3. More specifically, the impeller rotational torque generation section 3 of the centrifugal blood pump apparatus 50 does not have the rotor. Thus in the impeller rotational torque generation section 3, the impeller 21 is driven not by the rotor but by the stator coil 61.

The impeller 21 rotates without contacting the inner surface of the housing 20 owing to the hydrodynamic pressure generated by the hydrodynamic pressure groove during the rotation of the impeller 21. In the centrifugal blood pump apparatus 50, the electromagnet 41 attracts the impeller 21 in the direction opposite to the direction in which the stator coils 61 attracts the impeller 21. Therefore the impeller 21 rotates with the impeller 21 spaced at a longer distance from the housing than the housing-to-impeller distance provided by the action of the conventional hydrodynamic pressure groove.

The housing 20 has the blood inlet port 22 and the blood outlet port 23. The housing 20 is made of a nonmagnetic material. The housing 20 accommodates a blood chamber 24 communicating with the blood inlet port 22 and the blood outlet port 23. The housing 20 also accommodates the impeller 21 therein. The blood inlet port 22 projects substantially vertically from the vicinity of the center of the upper surface of the housing 20. As shown in FIGS. 3 and 12, the blood outlet port 23 projects tangentially from the side surface of the. substantially cylindrical housing 20.

As shown in FIG. 11, the disc-shaped impeller 21 having a through-hole in the center thereof is accommodated inside the blood chamber 24 formed inside the housing 20. As shown in FIG. 11, the impeller 21 includes an annular plate-shaped member (lower shroud) 27 forming the lower surface thereof, an annular plate-shaped member (upper shroud) 28 which forms the upper surface thereof and is open at the center thereof, and a plurality of vanes (seven) 18 formed between the lower shroud 27 and the upper shroud 28. A plurality of (seven) blood passages 26 partitioned from one another by the adjacent vanes 18 is formed between the lower shroud 27 and the upper shroud 28. As shown in FIG. 12, each of the blood passages 26 communicates with the center opening of the impeller 21 and extends from the center opening of the impeller 21 to its periphery, with each of the blood passages 26 becoming gradually larger in the width thereof. In other words, the vanes 18 are formed between the adjacent blood passages 26. In the embodiment, the vanes 18 and blood passages 26 are spaced at equiangular intervals respectively and formed in substantially the same shape respectively.

As shown in FIG. 12, a plurality (for example, 6 to 12) of the first magnetic materials 25 (permanent magnet, follower magnet) is embedded in the impeller 21. In this embodiment, the first magnetic materials 25 are embedded in the lower shroud 27. The first magnetic material (permanent magnet) 25 is provided so that the stator coils 61 of the impeller rotational torque generation section 3 to be described later attracts the impeller 21 toward the side opposite to the side where the blood inlet port 22 is disposed. That is, the first magnetic material 25 serves as a means for magnetically coupling the impeller 21 and the stator coil 61 to each other and transmitting the rotational torque from the impeller rotational torque generation section 3 to the impeller 21.

The magnetic coupling between the impeller 21 and the stator coil 61 which will be described later can be ensured by embedding a plurality of the first magnetic materials 25 in the impeller 21. It is preferable that each of the first magnetic materials 25 (permanent magnet) is approximately trapezoidal. Each of the first magnetic materials 25 may be ring-shaped or rectangular plate-shaped. It is preferable that the number of the first magnetic materials 25 corresponds to that of the stator coils 61 and that the arrangement mode of the first magnetic materials 25 corresponds to that of the stator coils 61. A plurality of the magnetic materials 25 is arranged on a circumference at equiangular intervals around the axis of the impeller 21, with positive poles and negative poles alternating with each other.

The impeller 21 further includes the second magnetic member 28 which itself constitutes the upper shroud or which is provided inside the upper shroud. In this embodiment, the entire upper shroud is formed of the second magnetic member 28. The second magnetic member 28 is provided so that the electromagnet 41 of the assistant impeller attraction section 4 attracts the impeller 21 toward the side opposite to the stator coil-disposed side, namely, toward the blood inlet port 22. The second magnetic member 28 is made of magnetic stainless steel.

The impeller 21 is attracted toward the stator coil-disposed side as well as the side opposite to the stator coil-disposed side by the electromagnet 41. Therefore the impeller 21 rotates inside the housing 20 with the impeller 21 spaced at the longer distance from the housing than the housing-to-impeller distance provided by the action of the conventional hydrodynamic pressure groove.

As shown in FIGS. 11 and 13, the impeller rotational torque generation section 3 includes a plurality of stator coils 61 accommodated in the housing 20. The stator coils 61 are arranged on a circumference substantially equiangularly around the axis of the circumference. Six multi-layer stator coils are used in the embodiment. A rotating magnetic field is generated by switching the direction of electric current flowing through stator coils 61. Owing to the generated rotating magnetic field, the impeller 21 is attracted to the stator coils 61 and rotates.

The construction of the assistant impeller attraction section 4 is the same as that of the assistant impeller attraction section of the centrifugal blood pump apparatus 1. Thus regarding the construction of the assistant impeller attraction section 4, the above description should be referred to.

In the centrifugal blood pump apparatus 50, the housing 20 has the inner surface 20a accommodating the impeller 21 and forming the blood chamber 24. The housing 20 has the hydrodynamic pressure groove 38 formed on a portion, of its inner surface 20a, disposed at its stator coil-disposed side. When the number of rotations of the impeller 21 becomes more than a predetermined number of rotations, a hydrodynamic bearing effect is generated between the hydrodynamic pressure groove 38 and the impeller 21. Thereby the impeller 21 rotates without contacting the inner surface 20a of the housing 20. The construction of the hydrodynamic pressure groove 38 is the same as that of the hydrodynamic pressure groove of the centrifugal blood pump apparatus 1. Thus regarding the construction of the hydrodynamic pressure groove 38, the above description should be referred to. The hydrodynamic pressure groove may be formed on the surface of the impeller 21 at its stator coil-disposed side instead of disposing it on the housing side. In this case, it is preferable that the hydrodynamic pressure groove has the same construction as that of the above-described hydrodynamic pressure groove. It is preferable that as shown in FIG. 7, a corner 38a of the hydrodynamic pressure groove 38 is chamfered to allow the corner 38a to have a radius of rounding at not less than 0.05 mm. Thereby it is possible to reduce generation of hemolysis.

In the centrifugal blood pump apparatus 50, similarly to the centrifugal blood pump apparatus 70 shown in FIGS. 17 and 18, the housing 20 may have a second hydrodynamic pressure groove formed on a portion, of its inner surface 20b, disposed at the electromagnet-disposed side thereof. The construction of the second hydrodynamic pressure groove is the same as that of the second hydrodynamic pressure groove of the centrifugal blood pump apparatus 70. Thus regarding the construction of the second hydrodynamic pressure groove, the above description should be referred to. The second hydrodynamic pressure groove may be disposed on the surface of the impeller 21 at its electromagnet-disposed side instead of disposing it on the housing side. In this case, it is preferable that the second hydrodynamic pressure groove has the same construction as that of the above-described hydrodynanic pressure groove. It is preferable that similarly to the hydrodynamic pressure groove shown in FIG. 7, a corner of the hydrodynamic pressure groove is chamfered to allow the corner to have a radius of rounding at not less than 0.05 mm. Thereby it is possible to reduce generation of hemolysis.

It is preferable to provide the centrifugal blood pump apparatuses with a control mechanism 6.

The control mechanism 6 of the centrifugal blood pump apparatus 1 will be described below with reference to FIGS. 1 and 9.

The control mechanism 6 of the centrifugal blood pump apparatus 1 of the embodiment shown in FIG. 1 has a power amplifier 52 for the motor 34 of the impeller rotational torque generation section 3, a motor control circuit 53, a motor current monitoring section 55, a power amplifier 54 for the electromagnet 41, an electromagnet control circuit 56, an electromagnet current monitoring section 57, and a control section 51. The control section 51 may have a motor current monitoring function.

The control mechanism 6 of the centrifugal blood pump apparatus 50 shown in FIG. 9 has a power amplifier 62 for the stator coil 61 of the impeller rotational torque generation section 3, a stator coil control circuit 63, a stator coil current monitoring section 64, a power amplifier 54 of the electromagnet 41, the electromagnet control circuit 56, the electromagnet current monitoring section 57, and the control section 51. The control section 51 may have a stator coil current monitoring function.

The control mechanism 6 controls the impeller rotational torque generation section 3 (motor or stator coil) and the electromagnet 41. It is preferable that the control mechanism 6 has a function of changing the degree of the impeller-attracting force of the electromagnet 41 according to a rotation speed generated by the impeller rotational torque generation section 3. It is preferable that the control mechanism 6 has a function of keeping the distance between the impeller 21 and the housing 20 constant by changing the degree of the impeller-attracting force of the electromagnet 41 according to the rotation speed generated by the impeller rotational torque generation section 3. It is preferable that the distance between the impeller 21 and the housing 20 is 50 to 150 µm. Each of the centrifugal blood pump apparatuses 1, 50 has a function of monitoring the electric current of the impeller rotational torque generation section 3. The control mechanism 6 controls the electromagnet by using a motor current value detected by the function of monitoring the electric current of the impeller rotational torque generation section 3.

The reason the degree of the impeller-attracting force of the electromagnet 41 is changed according to the rotation speed generated by the impeller rotational torque generation section 3 (motor or stator coil) is because a load capacity is generated by the hydrodynamic pressure groove. The load capacity is a term for a bearing and has a dimension of a force. The load capacity acts in the same direction as the direction in which the attractive force of the electromagnet acts. If the hydrodynamic pressure groove has a simple configuration such as a stepped groove, the load capacity is proportional to the viscosity of a fluid and the rotation speed generated by the impeller rotational torque generation section, according to a two-dimensional theoretical analysis (analysis which is made by considering only the configuration of a cross section of the hydrodynamic pressure groove and supposing that the longitudinal direction thereof orthogonal to the cross section thereof is much longer than the width of the cross section).

In the centrifugal blood pump apparatuses 1, 50, (1) the coupling force (generated by the permanent magnets in the centrifugal blood pump apparatus 1, and generated by the stator coil in the centrifugal blood pump apparatus 50) acts between the impeller and the motor; and (2) the attractive force acts owing to the attractive force of the electromagnet between the impeller and the electromagnet, and the load capacity acts owing to the action of the hydrodynamic pressure groove.

The impeller levitates inside the housing and rotates at a position where the force of (1) and the force of (2) balance with each other. It is preferable that the distance between the impeller and the housing is sufficiently short to prevent for generation of the hemolysis. It is necessary to make an electromagnet current high to make the housing-to-impeller distance long. To reduce an electric power, it is desirable that the housing-to-impeller distance is longer than that provided only by the hydrodynamic pressure groove and is allowably short. Thus it is necessary to control the impeller rotational torque generation section and the electromagnet so that the force of (1) and the force of (2) balance with each other at an allowable small value of the housing-to-impeller distance. That is, if the force of (1) is constant, it is necessary to make the force of (2) constant, even if the rotation speed generated by the impeller rotational torque generation section changes. The force of (2) is the sum of the attractive force of the electromagnet and the load capacity. Thus when the load capacity changes in dependence on the rotation speed generated by the impeller rotational torque generation section, the sum of the attractive force of the electromagnet and the load capacity is made constant by changing the attractive force of the electromagnet. Thereby it is possible to secure a desired levitation position of the impeller. More specifically, the load capacity in the force of (2) increases in dependence on the rotation speed generated by the impeller. Thus even though the degree of the attractive force of the electromagnet (in other words, electromagnet current) is reduced, it is possible to secure the desired levitation position and reduce a power consumption.

Results of the two-dimensional theoretical analysis performed supposing that the hydrodynamnic pressure groove has a simple configuration such as the stepped groove is described below.

Figure 15:
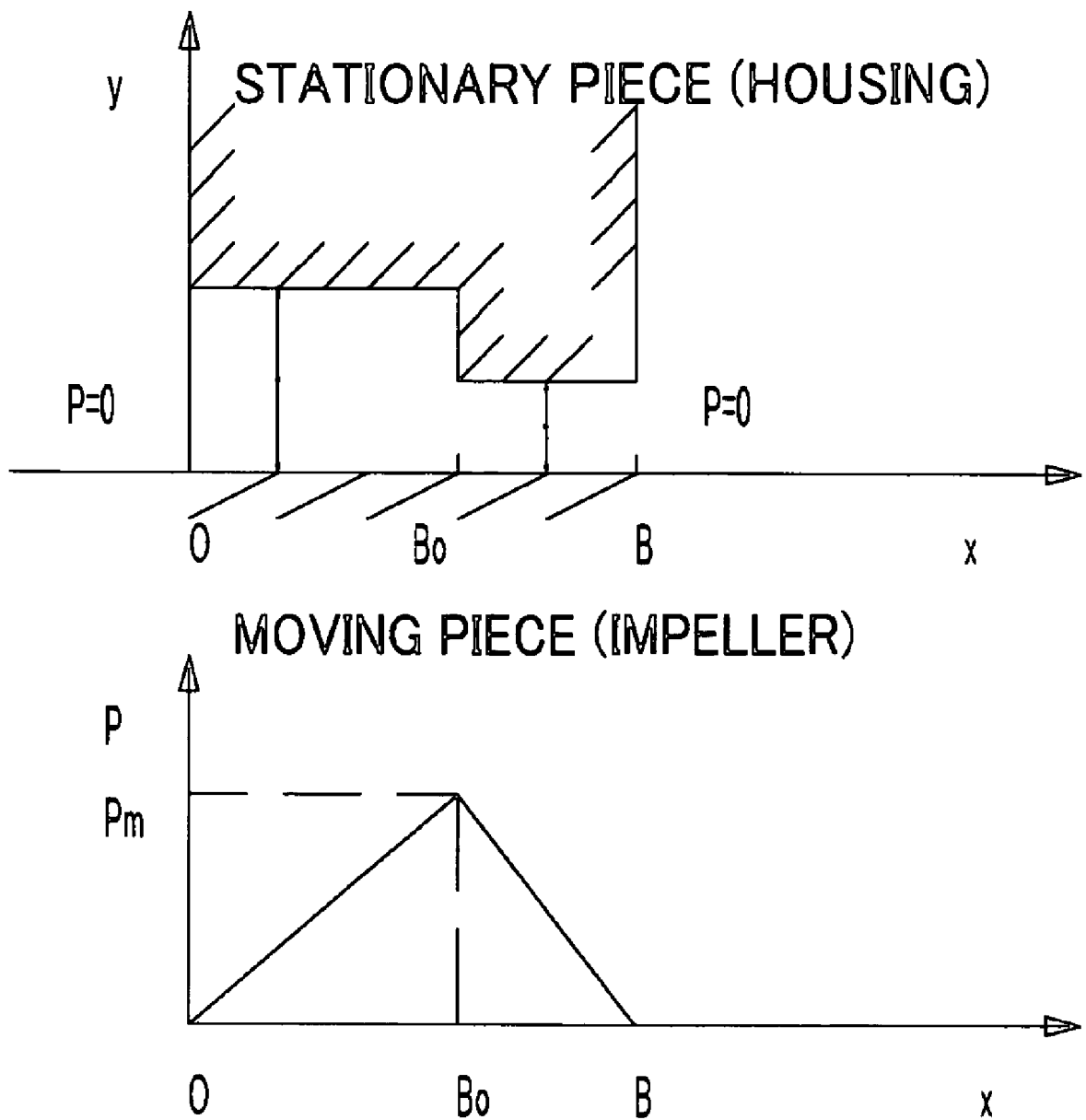
FIG. 15 is an explanatory for explaining the process of a two-dimensional theoretical analysis regarding a hydrodynamic pressure groove.

Supposing that the hydrodynamic pressure groove has a configuration (the length of the hydrodynamic pressure groove in the cross-sectional direction of the hydrodynamic pressure groove is L) shown in FIG. 15, a pressure p is expressed as follows:

In a region 1 (0<x<Bo): p =(Pm/Bo)x

In a region 2 (Bo<x<B): p=[Pm/(B−Bo)](B−x)

where the change of pressure p in the y-direction is sufficiently small and thus can be ignored.

Pm=6μU($h_1$−$h_2$)/[$h_1^3$/Bo+$h_2^3$(B−Bo)]

Where μ and U are the viscosity of a fluid and the radial velocity (proportional to the number of rotations) of the impeller respectively.

Therefore the load capacity W is expressed as follows:

W=L$\int_0^B$pdx=LBPm/2

The load capacity W is divided by μ $ULB^2$ to obtain the following dimensionless Wd-less:

Wd-less=W$h_2^2$/(μU$LB^2$)=3s)(1−s)/[$a^3$(1−s)+s]

where a and s are as follows:

a=$h_1$/$h_2$, s=Bo/B

Figure 16:
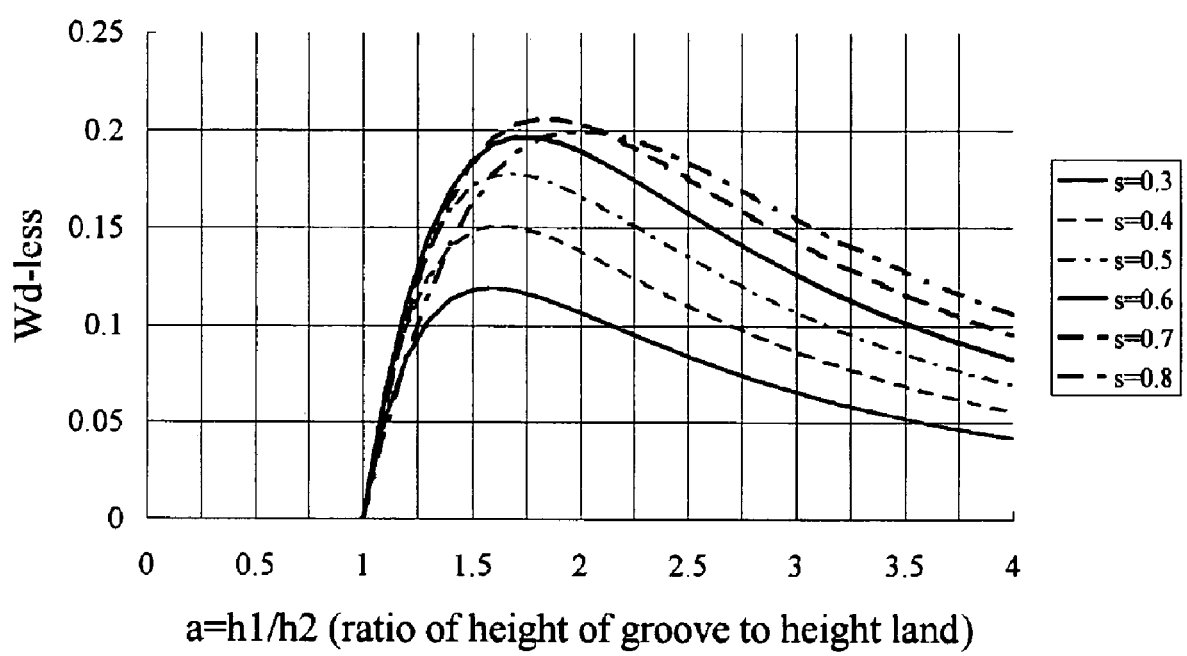
FIG. 16 is an explanatory for explaining the process of the two-dimensional theoretical analysis regarding the hydrodynamic pressure groove.

The change of Wd-less with respect to a and s is as shown in FIG. 16. It is understood that there is an efficient s (Bo/B) which provides a maximum load capacity when the height of the groove and the height of the land are set to desired $h_1$ and $h_2$ respectively. Therefore it is possible to obtain a sufficient load capacity by setting the following configuration parameters of the hydrodynamic pressure groove to a suitable value respectively. Consequently it is possible to provide a blood pump which consumes a small electric power owing to suppression of the degree of the attractive force of the electromagnet:

$h_1$–$h_2$
B, Bo, L

It is preferable that the control mechanism 6 has a rotation start state control function of starting the rotation of the impeller rotational torque generation section 3 with the electromagnet 41 attracting the impeller 21 thereto at a force not less than a predetermined value. It is preferable that in addition to this control function, the control mechanism 6 has a control function of reducing the attractive force of the electromagnet 41 to a value less than the predetermined value after the impeller rotational torque generation section 3 starts to operate. It is preferable that in dependence on the rotation speed generated by the impeller rotational torque generation section 3, this control function changes the impeller-attracting force of the electromagnet 41.

It is preferable that the control mechanism 6 has a function of detecting the state of failure of coupling between the impeller 21 and the impeller rotational torque generation section 3. It is preferable that the control mechanism 6 has also a function of re-coupling function of operating the electromagnet 41 and the impeller rotational torque generation section 3 after detecting the failure.

More specifically, the control section 51 has a failure detection function of determining whether the coupling between the impeller 21 and the impeller rotational torque generation section 3 has failed and the re-coupling function of operating the electromagnet 41 and the impeller rotational torque generation section 3 after detecting the failure. As an example of the re-coupling function, it is preferable that after the control section 51 detects the failure and the motor 34 and electromagnet 41 are suspended, the electromagnet 41 is actuated and then the rotation of the impeller rotational torque generation section 3 is started. The control section 51 stores a minimum current value of the impeller rotational torque generation section 3. If a detected current value thereof is lower than the stored current value, it is determined that the failure has occurred. It is possible to determine that the failure has occurred, when a detected current value of the impeller rotational torque generation section 3 is lower than a motor current value at a predetermined rotation speed generated by the impeller rotational torque generation section 3. More specifically, it is determined that the coupling between the impeller and the rotor has failed, when a detected motor current value is less than a reference motor current value (0.12 A) stored at a predetermined number of rotations (for example, 1000 rpm) of the motor, although an actual number of rotations of the motor is larger than the predetermined number of rotations (1000 rpm).

Figure 14:
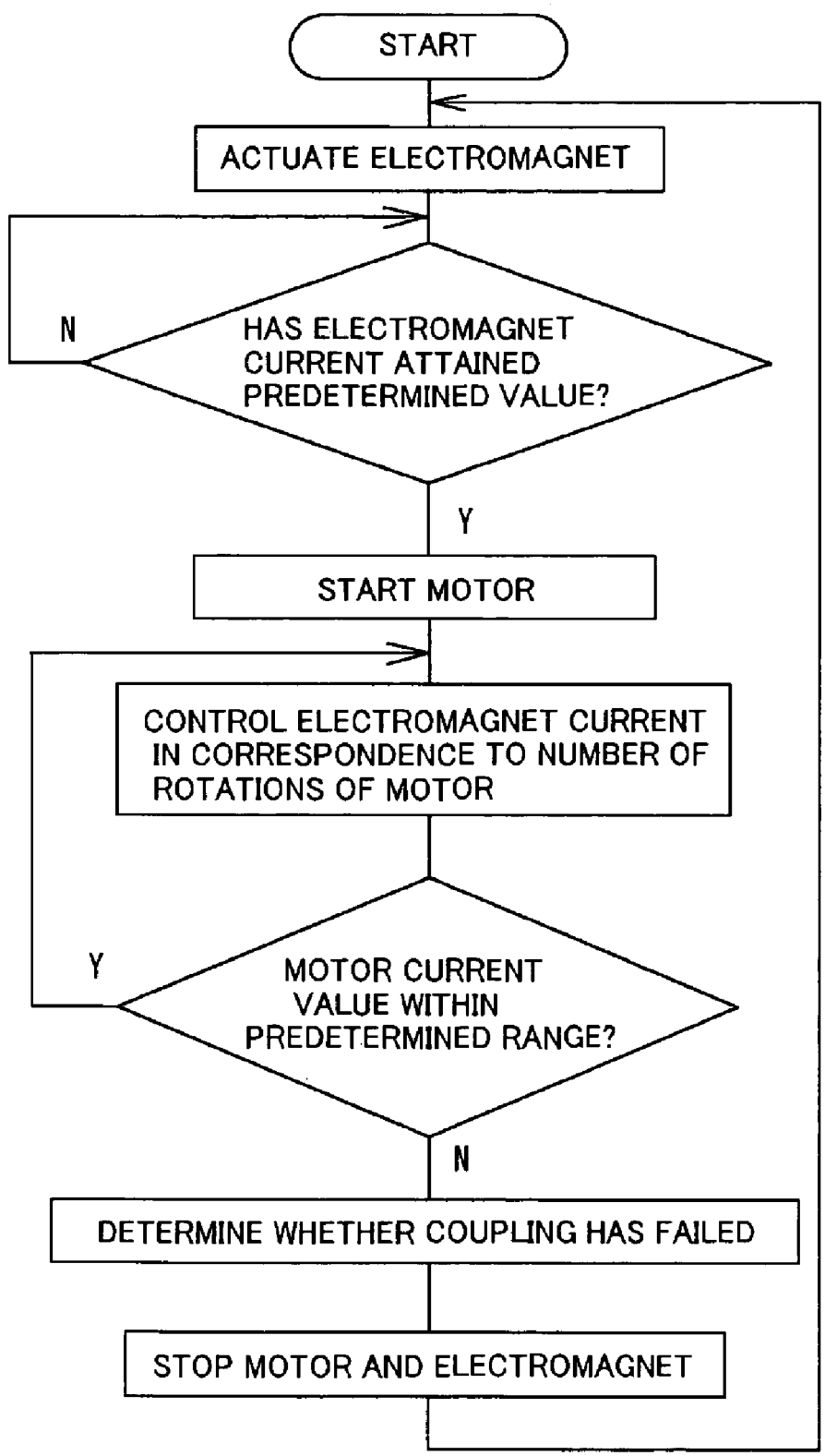
FIG. 14 is a flowchart for describing the operation of the centrifugal blood pump apparatus of an embodiment of the present invention.

The operation of the centrifugal blood pump apparatus 1 of this embodiment is described below with reference to the flowchart shown in FIG. 14.

When the centrifugal blood pump apparatus 1 starts to operate, initially the electromagnet 41 is actuated and applies an attractive force to the impeller 21. The attractive force is directed to the side opposite to the side where the impeller rotational torque generation section 3 (rotor or stator coil) is disposed. After an electromagnet current value attains a predetermined value, the impeller rotational torque generation section 3, namely, the motor starts to rotate. Thus the impeller 21 rotates. In applying electric current to the electromagnet, 41, the attractive force of the electromagnet 41 can be adjusted by changing the duty ratio of a square wave-shaped electric current. The control section 51 controls electromagnet current in correspondence to the rotation speed generated by the impeller rotational torque generation section 3. More specifically, the control section 51 lowers the electromagnet current by an amount corresponding to an excess amount over a predetermined distance of the impeller 21 from the inner surface of the housing owing to an increase of the load capacity caused by an increase of the number of rotations of the impeller 21. Thereby the control section 51 reduces the attractive force to be exerted on the impeller 21 by the electromagnet 41. In addition to the control of the electromagnet current, the control section 51 is always detecting whether the motor current value falls within the predetermined range. If the motor current value is out of the predetermined range, the control section 51 determines that the failure has occurred, thus suspending the operation of the motor 34 and the electromagnet 41. Thereafter only the electromagnet 41 is operated to perform a normal operation.

The centrifugal blood pump apparatus of the present invention has a housing having a fluid inlet port and a fluid outlet port, a centrifugal pump section including an impeller having a first magnetic material therein and rotating inside the housing to feed a fluid by a centrifugal force generated during a rotation thereof, an impeller rotational torque generation section for attracting and rotating the impeller, and a hydrodynamic pressure groove formed at a portion of an inner surface of the housing at a rotor-disposed side or at a portion of a surface of the impeller at the rotor-disposed side. The impeller rotates without contacting the housing owing to an action of the hydrodynamic groove. The centrifugal blood pump apparatus further includes an electromagnet for attracting the first magnetic material of the impeller or a second magnetic material provided on the impeller separately from the first magnetic material in a direction opposite to a direction in which the impeller rotational torque generation section attracts the first magnetic material and helping the impeller levitate.

Therefore in the centrifugal blood pump apparatus in which the impeller is rotated without contacting the housing by utilizing the action of the hydrodynamic pressure groove, it is possible to assist the levitation of the impeller effectively and secure a predetermined distance between the impeller and the housing. Thereby it is possible to reduce generation of hemolysis. Further unlike the centrifugal blood pump apparatus of the magnetic levitation type, it is unnecessary to provide the centrifugal blood pump apparatus with a position sensor. Thereby the centrifugal blood pump apparatus can be made compact and consumes a small electric power.

The centrifugal blood pump apparatus includes the control mechanism for controlling the motor and the electromagnet. The control mechanism has a function of changing the degree of the impeller-attracting force of the electromagnet according to the rotation speed generated by the impeller rotational torque generation section. This construction saves an electric power and secures a housing-to-impeller distance in which hemolysis occurs very little.

The control mechanism has a function of keeping the distance between the impeller and the housing constant by changing the degree of the impeller-attracting force of the electromagnet according to the rotation speed generated by the impeller rotational torque generation section. This construction saves an electric power and secures a housing-to-impeller distance in which hemolysis occurs very little.

The control mechanism has the rotation start state control function of starting the rotation of the impeller rotational torque generation section with the electromagnet attracting the impeller thereto at a force not less than a predetermined value. This construction accomplishes a preferable start of rotation of the impeller and prevents hemolysis of blood present between the impeller and the housing at an initial time of the rotation of the impeller.

The control mechanism has the rotation start state control function of starting the rotation of the impeller rotational torque generation section with the electromagnet attracting the impeller thereto at a force not less than the predetermined value; and the control function of reducing the attractive force of the electromagnet to a value less than the predetermined value after the impeller rotational torque generation section starts to operate. This construction accomplishes a preferable start of rotation of the impeller and prevents hemolysis of blood present between the impeller and the housing at an initial time of the rotation of the impeller. This construction also saves an electric power and secures a housing-to-impeller distance in which hemolysis occurs very little.

What is claimed is:

1. A centrifugal blood pump apparatus comprising:
   a housing having a fluid inlet port and a fluid outlet port;
   a centrifugal pump section including an impeller having a first magnetic material therein and rotatable inside said housing to feed a fluid by a centrifugal force generated during a rotation thereof;
   an impeller rotational torque generation section for attracting and rotating said impeller;
   and a hydrodynamic pressure groove formed at a portion of an inner surface of said housing at an impeller rotational torque generation section side or at a portion of a surface of said impeller at said impeller rotational torque generation section side,
   said impeller being rotatable without contacting said housing owing to an action of said hydrodynamic groove,
   an electromagnet for attracting said first magnetic material of said impeller or a second magnetic material provided on said impeller separately from said first magnetic material in a direction opposite to a direction in which said impeller rotational torque generation section attracts said first magnetic material and helping said impeller levitate;
   a control mechanism for controlling said impeller rotational torque generating section and said electromagnet, said control mechanism starting rotation of said impeller rotational torque generating section with said electromagnet attracting said impeller thereto at a force not less than a predetermined value; and
   wherein said impeller rotational torque generation section has a rotor having a magnet for attracting said first magnetic material of said impeller and a motor for rotating said rotor; and said hydrodynamic pressure groove formed at the portion of the inner surface of said housing at a rotor-disposed side or the portion of the surface of said impeller at said rotor-disposed side, and said electromagnet attracting said first magnetic material or the second magnetic material in a direction opposite to the direction in which said magnet of said rotor attracts said first magnetic material to help said impeller levitate.

2. A centrifugal blood pump apparatus according to claim 1, wherein said first magnetic material of said impeller and said magnet of said rotor for attracting said first magnetic material comprise a plurality of permanent magnets respectively; and said permanent magnets of said impeller are arranged in first and second different circumferential arrangements, and said permanent magnets of said rotor are arranged in first and second different circumferential arrangements, said permanent magnets forming the first circumferential arrangement of said permanent magnets of said impeller and the first circumferential arrangement of said permanent magnets of said rotor facing each other with opposite polarities, said permanent magnets forming the second circumferential arrangement of said permanent magnets of said impeller and the second circumferential arrangement of said permanent magnets of said rotor facing each other with opposite.

3. A centrifugal blood pump apparatus according to claim 1, wherein said impeller rotational torque generation section has a plurality of stator coils, disposed circumferentially to rotate said impeller, for attracting said first magnetic material of said impeller of said centrifugal blood pump section; and said hydrodynamic pressure groove being formed at the portion of the inner surface of said housing at a stator coil-disposed side or at the portion of the surface of said impeller at said stator coil-disposed side thereof, and said electromagnet attracting said first magnetic material or the second magnetic material in a direction opposite to the direction in which said stator coils attract said first magnetic material and helping said impeller levitate.

4. A centrifugal blood pump apparatus according to claim 1, wherein the control mechanism changes a degree of an impeller-attracting force of said electromagnet according to a rotation speed generated by said impeller rotational torque generation section.

5. A centrifugal blood pump apparatus according to claim 4, wherein said control mechanism maintains a constant distance between said impeller and said housing by changing the degree of the impeller-attracting force of said electromagnet according to the rotation speed generated by said impeller rotational torque generation section.

6. A centrifugal blood pump apparatus according to claim 4, wherein said control mechanism monitors electric current of said impeller rotational torque generation section and controls said electromagnet by using an electric current value detected by said control mechanism.

7. A centrifugal blood pump apparatus according to claim 1, wherein the control mechanism reduces an attractive force of said electromagnet to a value less than said predetermined value after said impeller rotational torque generation section starts to rotate.

8. A centrifugal blood pump apparatus according to claim 1, wherein a corner of said hydrodynamic pressure groove is chamfered to allow said corner to have a radius of rounding at not less than 0.05 mm.

9. A centrifugal blood pump apparatus according to claim 1, wherein said centrifugal blood pump apparatus has a second hydrodynamic pressure groove formed at a portion of an inner surface of said housing at a electromagnet-disposed side or at a portion of a surface of said impeller at said electromagnet-disposed side.

10. A centrifugal blood pump apparatus according to claim 9, wherein a corner of said second hydrodynamic pressure groove is chamfered to allow said corner to have a radius of rounding at not less than 0.05 mm.

11. A centrifugal blood pump apparatus comprising:
a housing having a fluid inlet port and a fluid outlet port;
a centrifugal pump section including an impeller having a first magnetic material therein and rotatable inside said housing to feed a fluid by a centrifugal force generated during a rotation thereof;
an impeller rotational torque generation section for attracting and rotating said impeller;
and a hydrodynamic pressure groove formed at a portion of an inner surface of said housing at an impeller rotational torque generation section side or at a portion of a surface of said impeller at said impeller rotational torque generation section side,
said impeller being rotatable without contacting said housing owing to an action of said hydrodynamic groove,
an electromagnet for attracting said first magnetic material of said impeller or a second magnetic material provided on said impeller separately from said first magnetic material in a direction opposite to a direction in which said impeller rotational torque generation section attracts said first magnetic material and helping said impeller levitate; and
a control mechanism for controlling said impeller rotational torque generating section and said electromagnet, said control mechanism starting rotation of said impeller rotational torque generating section with said electromagnet attracting said impeller thereto at a force not less than a predetermined value; and
wherein said impeller rotational torque generation section has a plurality of stator coils, disposed circumferentially to rotate said impeller, for attracting said first magnetic material of said impeller of said centrifugal blood pump section; and said hydrodynamic pressure groove being formed at the portion of the inner surface of said housing at a stator coil-disposed side or at the portion of the surface of said impeller at said stator coil-disposed side thereof, and said electromagnet attracting said first magnetic material or the second magnetic material in a direction opposite to the direction in which said stator coils attract said first magnetic material and helping said impeller levitate.

12. A centrifugal blood pump apparatus comprising:
a housing having a fluid inlet port and a fluid outlet port;
a centrifugal pump section including an impeller having a first magnetic material therein and rotatable inside said housing to feed a fluid by a centrifugal force generated during a rotation thereof;
an impeller rotational torque generation section for attracting and rotating said impeller;
and a hydrodynamic pressure groove formed at a portion of an inner surface of said housing at an impeller rotational torque generation section side or at a portion of a surface of said impeller at said impeller rotational torque generation section side;
said impeller being rotatable without contacting said housing owing to an action of said hydrodynamic groove;
an electromagnet for attracting said first magnetic material of said impeller or a second magnetic material provided on said impeller separately from said first magnetic material in a direction opposite to a direction in which said impeller rotational torque generation section attracts said first magnetic material and helping said impeller levitate;
a control mechanism for controlling said impeller rotational torque generating section and said electromagnet, said control mechanism starting rotation of said impeller rotational torque generating section with said electromagnet attracting said impeller thereto at a force not less than a predetermined value; and
wherein said centrifugal blood pump apparatus has a second hydrodynamic pressure groove formed at a portion of an inner surface of said housing at a electromagnet-disposed side or at a portion of a surface of said impeller at said electromagnet-disposed side.

* * * * *

UNITED STATES PATENT AND TRADEMARK OFFICE
CERTIFICATE OF CORRECTION

PATENT NO. : 7,470,246 B2  
APPLICATION NO. : 10/736610  
DATED : December 30, 2008  
INVENTOR(S) : Takehisa Mori et al.

Page 1 of 1

It is certified that error appears in the above-identified patent and that said Letters Patent is hereby corrected as shown below:

Column 7, Line 35: change "comer" to --corner--.

Column 11, Line 24: change "hydrodynanic" to --hydrodynamic--.

Column 13, Line 21:

Change "$Wd\text{-less}=Wh_2^2/(\mu ULB^2)=3s)(1-s)/[a^3(1-s)+s]$"

To --$Wd\text{-less}=Wh_2^2/(\mu\ ULB^2)=3s)(1-s)(a-1)/[a^3(1-s)+s]$--.

Signed and Sealed this

Sixteenth Day of June, 2009

JOHN DOLL  
*Acting Director of the United States Patent and Trademark Office*